US012661159B1

(12) United States Patent
Kaufmann et al.

(10) Patent No.: US 12,661,159 B1
(45) Date of Patent: Jun. 23, 2026

(54) ORTHOPEDIC ANCHOR SYSTEM

(71) Applicant: Genesys Orthopedic Systems, L.L.C., Austin, TX (US)

(72) Inventors: Josh Kaufmann, Austin, TX (US); Landon Gilkey, Austin, TX (US); Greg Calbert, Austin, TX (US); Scott Bryant, Austin, TX (US); Maahir Haque, Orlando, FL (US); Scott L. Parker, Nashville, TN (US); Bill Sowers, Austin, TX (US)

(73) Assignee: Genesys Orthopedic Systems, L.L.C., Austin, TX (US)

( * ) Notice: Subject to any disclaimer, the term of this patent is extended or adjusted under 35 U.S.C. 154(b) by 0 days.

(21) Appl. No.: 19/272,133

(22) Filed: Jul. 17, 2025

(51) Int. Cl.
  *A61B 17/70* (2006.01)

(52) U.S. Cl.
  CPC ...... *A61B 17/7055* (2013.01); *A61B 17/7034* (2013.01)

(58) Field of Classification Search
  CPC ..................... A61B 17/7055; A61B 17/7034
  See application file for complete search history.

(56) References Cited

U.S. PATENT DOCUMENTS

| | | | |
|---|---|---|---|
| 6,565,566 | B1 | 5/2003 | Wagner et al. |
| 6,981,976 | B1 | 1/2006 | Schoenefeld |
| 7,699,872 | B2 | 4/2010 | Farris et al. |
| 7,833,252 | B2 | 11/2010 | Justis et al. |
| 7,942,911 | B2 | 5/2011 | Doubler et al. |
| 8,292,932 | B2 * | 10/2012 | Matthis .............. A61B 17/8625 |
| | | | 606/313 |
| 8,343,201 | B2 | 1/2013 | Biyani et al. |
| 8,486,121 | B2 | 7/2013 | Biedermann et al. |
| 8,491,639 | B2 | 7/2013 | James et al. |
| 8,491,641 | B2 | 7/2013 | Nihalani |
| 8,523,918 | B2 | 9/2013 | Ainsworth et al. |
| 8,562,651 | B2 | 10/2013 | Metcalf et al. |
| 8,602,782 | B2 * | 12/2013 | Lomicka ................ A61C 8/006 |
| | | | 433/174 |
| 8,951,295 | B2 | 2/2015 | Matityahu et al. |
| 8,998,923 | B2 | 4/2015 | Chirico et al. |
| 9,445,848 | B2 * | 9/2016 | Anderson .......... A61B 17/7071 |
| 9,603,632 | B1 | 3/2017 | Gunn et al. |
| 9,717,538 | B2 | 8/2017 | Chin et al. |
| 9,743,961 | B2 | 8/2017 | Goel et al. |
| 9,757,114 | B2 | 9/2017 | McDevitt et al. |
| 9,820,780 | B2 | 11/2017 | Duncan et al. |
| 9,848,892 | B2 | 12/2017 | Biedermann et al. |
| 10,010,361 | B2 | 7/2018 | Biedermann et al. |

(Continued)

FOREIGN PATENT DOCUMENTS

| | | |
|---|---|---|
| CN | 209347198 U | 9/2019 |
| CN | 114848123 A | 8/2022 |

(Continued)

OTHER PUBLICATIONS

International Searching Authority, International Search Report and Written Opinion dated Apr. 30, 2024 in International Application No. PCT/US24/10826 (13 pages).

(Continued)

*Primary Examiner* — Tessa M Matthews
(74) *Attorney, Agent, or Firm* — Trop, Pruner & Hu, P.C.

(57) ABSTRACT

An embodiment includes a sacroiliac joint bone anchor system.

21 Claims, 35 Drawing Sheets

(56) References Cited

U.S. PATENT DOCUMENTS

| | | | |
|---|---|---|---|
| 10,149,709 | B2 | 12/2018 | Crawford et al. |
| 10,194,950 | B2 | 2/2019 | Felix et al. |
| 10,335,216 | B2 | 7/2019 | Mari et al. |
| 10,363,073 | B2 | 7/2019 | Raina et al. |
| 10,413,332 | B2 | 9/2019 | Schumacher et al. |
| 10,441,318 | B2 | 10/2019 | Donner et al. |
| 10,449,032 | B2 | 10/2019 | Paulk et al. |
| 10,517,645 | B2 | 12/2019 | van der Pol |
| 10,631,905 | B2 | 4/2020 | Asfora et al. |
| 10,675,074 | B2 | 6/2020 | Roby et al. |
| 10,736,683 | B2 | 8/2020 | Garvey |
| 10,905,482 | B2 | 2/2021 | Biedermann et al. |
| 10,905,484 | B2 | 2/2021 | McClintock |
| 10,932,838 | B2 | 3/2021 | Mehl et al. |
| 10,932,841 | B2 | 3/2021 | Grizzard et al. |
| 11,000,316 | B2 | 5/2021 | Jimenez |
| 11,129,655 | B2 | 9/2021 | Crossgrove et al. |
| 11,160,591 | B2 | 11/2021 | Biedermann et al. |
| 11,191,581 | B2 | 12/2021 | Koller et al. |
| 11,202,659 | B2 | 12/2021 | Cormier et al. |
| 11,234,738 | B2 | 2/2022 | Jackson et al. |
| 11,234,830 | B2 | 2/2022 | Mesiwala et al. |
| 11,337,735 | B2 | 5/2022 | Jackson et al. |
| 11,364,060 | B2 | 6/2022 | Arnin |
| 11,471,203 | B2 | 10/2022 | Sutika |
| 11,534,210 | B2 | 12/2022 | Dejardin |
| 11,653,962 | B2 | 5/2023 | Mohar et al. |
| 11,672,570 | B2 | 6/2023 | Stuart et al. |
| 11,678,997 | B2 | 6/2023 | Mesiwala et al. |
| 11,684,395 | B2 | 6/2023 | Loftis et al. |
| 11,730,526 | B2 | 8/2023 | Jackson et al. |
| 11,771,482 | B2 | 10/2023 | Kuntz et al. |
| 11,793,553 | B2 | 10/2023 | Jackson et al. |
| 11,813,172 | B2 | 11/2023 | Tanaka et al. |
| 11,849,984 | B2 | 12/2023 | Vrionis et al. |
| 11,883,077 | B2 | 1/2024 | Kaufmann et al. |
| 11,890,042 | B2 | 2/2024 | Peterson et al. |
| 11,896,275 | B2 | 2/2024 | Biedermann et al. |
| 11,957,391 | B2 | 4/2024 | Rezach et al. |
| 11,957,392 | B2 | 4/2024 | Lee et al. |
| 11,974,791 | B1 | 5/2024 | Robbins |
| 11,992,409 | B2 | 5/2024 | Patel |
| 11,992,410 | B1 | 5/2024 | Moseley et al. |
| 12,048,466 | B2 | 7/2024 | Suddaby |
| 12,064,156 | B2 | 8/2024 | Krumme et al. |
| 12,076,251 | B2 | 9/2024 | Mesiwala et al. |
| 12,082,859 | B2 | 9/2024 | Biedermann |
| 12,102,357 | B2 | 10/2024 | Jackson |
| 12,144,524 | B2 | 11/2024 | Allen et al. |
| 12,285,200 | B2 | 4/2025 | Geist et al. |
| 2006/0155278 | A1* | 7/2006 | Warnick .............. A61B 17/7037 |
| | | | 606/279 |
| 2007/0066977 | A1 | 3/2007 | Assell et al. |
| 2008/0147126 | A1 | 6/2008 | Tipirneni et al. |
| 2010/0082071 | A1 | 4/2010 | Moumene |
| 2011/0106173 | A1 | 5/2011 | Lindemann et al. |
| 2011/0288599 | A1 | 11/2011 | Michielli et al. |
| 2013/0053901 | A1 | 2/2013 | Cormier et al. |
| 2014/0031934 | A1 | 1/2014 | Trieu |
| 2014/0163624 | A1 | 6/2014 | Siegal et al. |
| 2014/0276846 | A1 | 9/2014 | Mauldin et al. |
| 2015/0327902 | A1* | 11/2015 | Eekhoff .............. A61B 17/8891 |
| | | | 606/310 |
| 2016/0310188 | A1 | 10/2016 | Marino et al. |
| 2017/0020573 | A1 | 1/2017 | Cain et al. |
| 2017/0086887 | A1 | 3/2017 | Bush, Jr. |
| 2020/0100822 | A1 | 4/2020 | Lipow |
| 2021/0228361 | A1 | 7/2021 | Petric et al. |
| 2022/0280200 | A1 | 9/2022 | Mickiewicz et al. |
| 2022/0387185 | A1 | 12/2022 | Stalcup et al. |
| 2023/0000526 | A1 | 1/2023 | Follini et al. |
| 2023/0165613 | A1 | 6/2023 | Miller et al. |
| 2023/0210667 | A1 | 7/2023 | Lindsey et al. |
| 2024/0180707 | A1 | 6/2024 | Peretz et al. |
| 2024/0252212 | A1 | 8/2024 | Jackson et al. |
| 2024/0374390 | A1 | 11/2024 | Kowalski |
| 2025/0057639 | A1 | 2/2025 | Stuart et al. |
| 2025/0064596 | A1 | 2/2025 | Park |
| 2025/0221743 | A1 | 7/2025 | Leff et al. |

FOREIGN PATENT DOCUMENTS

| | | |
|---|---|---|
| CN | 115517752 B | 12/2022 |
| DE | 102010042930 A1 | 4/2012 |
| DE | 102014107495 A1 | 12/2015 |
| DE | 102013001933 B4 | 9/2017 |
| EP | 1997450 B1 | 10/2011 |
| EP | 1799135 B1 | 3/2015 |
| EP | 3085320 B1 | 4/2022 |
| JP | H06125918 A | 5/1994 |
| JP | 2021529583 A | 11/2021 |
| WO | 2013138151 A2 | 9/2013 |
| WO | 2014088522 A2 | 6/2014 |
| WO | 2015095965 A1 | 7/2015 |
| WO | 2022245335 A1 | 11/2022 |
| WO | 2024151594 A1 | 7/2024 |

OTHER PUBLICATIONS

Alan et al. "Bilateralsacroiliac joint fusion in long constructs using self-harvesting porous S2-alar iliacscrews with an integrated tulip: technical considerations and early clinical andradiographic experience", Neurosurgical Focus 55, 1 (2023).

"Lateral Sacroiliac Joint Fusion—Slros® 3D Printed," genesysspine. com. Oct. 19, 2021, retrieved from https://web.archive.org/web/ 20211019093053/https://www.genesysspine.com/products/sacral/ lateral-sacroiliac-joint-fusion-siros-3d-printed/.

"Reunion: Sacroiliac Joint Fusion System," asturamedical. com, retrieved from https://asturamedical.com/product/reunion/.

"3D Printed Screw & Rod System," tsunamimedical.com. Accessed: Jul. 30, 2024, retrieved from https://web.archive.org/web/ 20240730074026/https://www.tsunamimedical.com/wp-content/ uploads/2022/10/BROCHURE-VENTOTENE-FIXED-SCREWS-STANDARD-54-45.pdf.

"Creo Amp® Stabilization System," globusmedical.com. Aug. 9, 2020 retrieved from https://web.archive.org/web/20200809110745/ https://www.globusmedical.com/products/creo-amp/.

"CD Horizon™ ModuLeX™ 5.5 Spinal System," Medtronic.com. Accessed: Jul. 30, 2024, retrieved from https://web.archive.org/web/ 20240730075004/https://www.medtronic.com/content/dam/medtronic-com/us-en/hcp/therapies-conditions/spinal-orthopaedic/spine-.

"Centerline Modular," lifespine.com. Jun. 4, 2020, downloaded from https://web.archive.org/web/20200604014344/https://lifespine. com/centerline/.

"Canaveral Modular Screws," thespinemarketgroup.com. Accessed: Jul. 30, 2024, downloaded from https://web.archive.org/web/ 20240730080019/https://thespinemarketgroup.com/wp-content/ uploads/2022/01/Canaveral-Modular-Brochure.Flospine.pdf.

U.S. Appl. No. 19/146,293, filed Jul. 8, 2025, entitled "Orthopedic Anchor System".

"I-Fuse", downloaded from https://web.archive.org/web/ 20250715220544/https://www.nsmedicaldevices.com/company-news/ si-bone-secures-fda-nod-for-rod-compatibility-with-ifuse-bedrock-granite/, on Jul. 15, 2025.

Kim et al., "A Novel Technique for Sacropelvic Fixation Using Image-Guided Sacroiliac Screws: A Case Series and Biomechanical Study", The Journal of Biomedical Research, 2019, 33(3).

"Surgical Technique", downloaded from https://web.archive.org/ web/20250715222233/https://www.aaos.org/videos/video-detail-page/26961_Videos on Jul. 15, 2025.

International Searching Authority, International Search Report and Written Opinion dated Apr. 14, 2026 in International Application No. PCT/US2025/038106 (11 pages).

* cited by examiner

101

320

321

513

513'

863

864

ORTHOPEDIC ANCHOR SYSTEM

TECHNICAL FIELD

Embodiments of the invention are in the field of orthopedic implants.

BACKGROUND

The sacroiliac joint (SI joint) is a joint in the pelvis that
connects the sacrum and the ilium. When ligaments of the
joint become loose or otherwise dysfunctional the SI joint
may fail to provide adequate shock absorption for the spine,
which may be painful. SI joint fusion is a technique used to
stabilize the SI joint and to alleviate pain caused by the
dysfunctional joint. One surgical technique includes placing
bone graft within the joint and then driving one or more
compression screws across the joint to stabilize the joint.
This may eventually lead to fusion of the joint and, ideally,
less pain.

BRIEF DESCRIPTION OF THE DRAWINGS

Features and advantages of embodiments of the present
invention will become apparent from the appended claims,
the following detailed description of one or more example embodiments, and the corresponding figures. Where con-
sidered appropriate, reference labels have been repeated
among the figures to indicate corresponding or analogous
elements.

FIGS. 3B and 3C cross-sectional views the
embodiment of FIG. 3A.

FIGS. 7C and
7D show perspective views of an embodiment (such as the
shorter embodiment of FIG. 7B) including a tulip.

FIG. 8H
provides a close up perspective view of a distal end of the
embodiment of FIG. 8A.

DETAILED DESCRIPTION

Figure 1A:
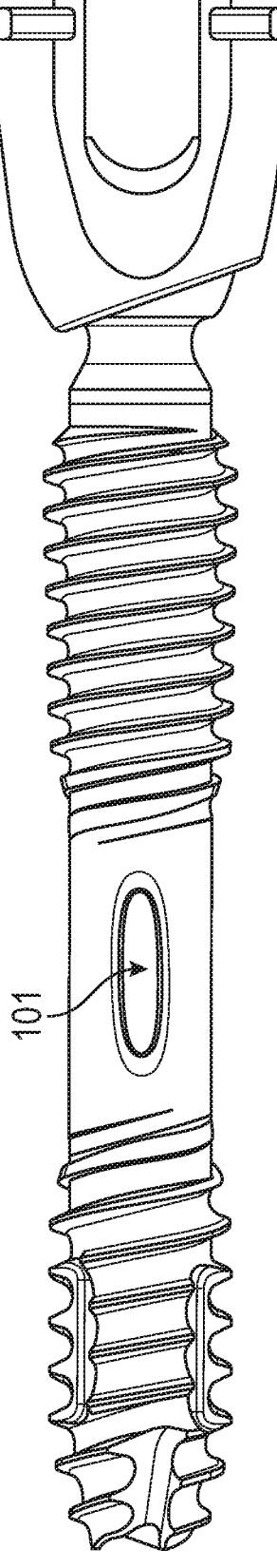
FIGS. 1A, 1B provide differing views of an embodiment.
FIGS. 2A, 2B provide differing views of an embodiment.
Figure 1B:
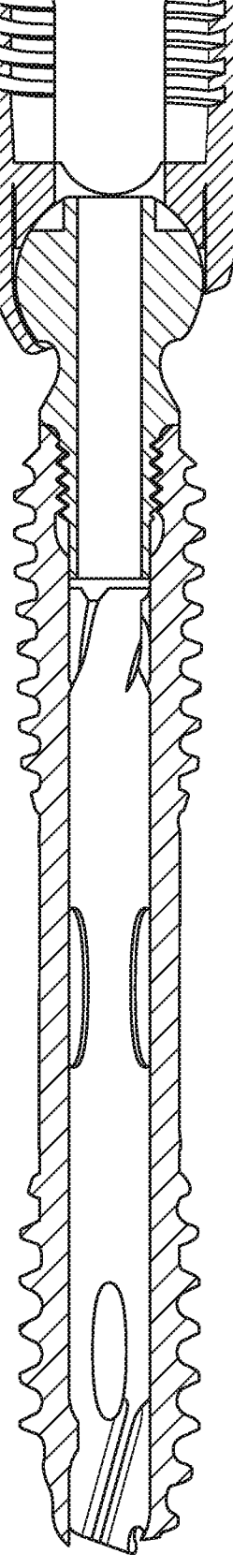
Figure 2A:
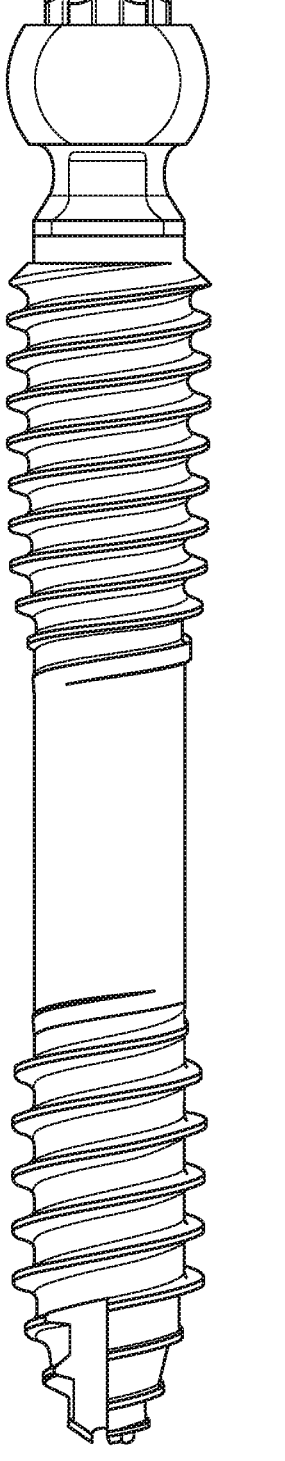
Figure 2B:
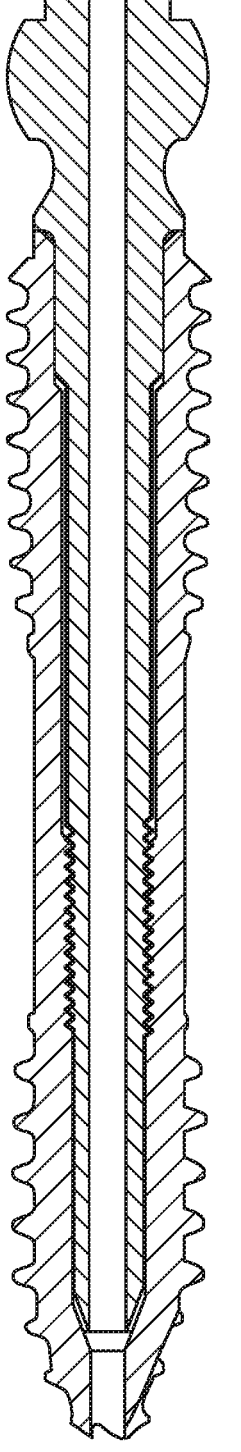

Reference will now be made to the drawings wherein like
structures may be provided with like suffix reference des-
ignations. In order to show the structures of various embodiments more clearly, the drawings included herein are dia-
grammatic representations of structures. Thus, the actual
appearance of the fabricated structures, for example in a
photo, may appear different while still incorporating the
claimed structures of the illustrated embodiments. More-
over, the drawings may only show the structures useful to
understand the illustrated embodiments. Additional struc-
tures known in the art may not have been included to
maintain the clarity of the drawings. "An embodiment",
"various embodiments" and the like indicate embodiment(s)
so described may include particular features, structures, or
characteristics, but not every embodiment necessarily
includes the particular features, structures, or characteristics.
Some embodiments may have some, all, or none of the
features described for other embodiments. "First", "second",
"third" and the like describe a common object and indicate
different instances of like objects are being referred to. Such
adjectives do not imply objects so described must be in a
given sequence, either temporally, spatially, in ranking, or in
any other manner. "Connected" may indicate elements are in
direct physical contact with each other and "coupled" may
indicate elements co-operate or interact with each other, but
they may or may not be in direct physical contact. Phrases
such as "comprising at least one of A and B" include
situations with A, B, or A and B.

An embodiment provides an anchor. One example of an
anchor is a screw. Other examples include nails and the like.

As shown in FIGS. 3A-3H, an embodiment includes a
bone anchor system comprising a sleeve (301) that includes
a central sleeve channel (302) that traverses the sleeve and
extends from a proximal end (303) of the sleeve to a distal
end (304) of the sleeve. The sleeve further includes first
(305) and second (306) threaded portions on an outer surface
of the sleeve, and a non-threaded portion (307) on the outer
surface of the sleeve and existing between the first and
second threaded portions. The sleeve includes a central
sleeve axis (308) that extends from the proximal end of the
sleeve to the distal end of the sleeve. The sleeve includes a
plurality of linear projections (309) on a wall of the central
sleeve channel.

The system further includes a rod or shaft (310) that
includes a central rod channel (311) that traverses the rod
and extends from a proximal end of the rod to a distal end
of the rod. The rod includes a head (312) on the proximal
end of the rod, the head including a circular cross-section.
The rod includes a central rod axis that extends from the
proximal end of the rod to the distal end of the rod. The rod
includes a plurality of linear slots (313) on an outer surface
of the rod. The rod is proportioned to slide within the central
sleeve channel, and the plurality of linear projections is
proportioned to slide within the plurality of linear slots.

An alternative embodiment includes a bone anchor sys-
tem comprising a sleeve (301) that includes: (a) a central
sleeve channel (302) that traverses the sleeve and extends
from a proximal end (303) of the sleeve to a distal end (304)
of the sleeve, (b) first (305) and second (306) threaded
portions on an outer surface of the sleeve, (c) a central sleeve
axis (308) that extends from the proximal end of the sleeve
to the distal end of the sleeve, and (e) a plurality of linear
projections (309) on a wall of the central sleeve channel. The
system further includes a rod (310) that includes: (a) a
central rod channel (311) that traverses the rod and extends
from a proximal end of the rod to a distal end of the rod, (b)
a head (312) on the proximal end of the rod, the head
including a circular cross-section; (c) a central rod axis that
extends from the proximal end of the rod to the distal end of
the rod, and (e) a plurality of linear slots (313) on an outer surface of the rod. The rod is proportioned to slide within the central sleeve channel, and the plurality of linear projections is proportioned to slide within the plurality of linear slots.

Thus, for example, not all embodiments necessarily include non-threaded portion 307. Some embodiments may extend threads 305 or 306 into areas 307. Other embodiments may include a set of threads with a pitch that differs from the pitch of threads of either or both of threads 305, 306.

Fenestrations (i.e., apertures, holes) may be included in smooth or threaded areas of the sleeve and/or rod. In some embodiments, fenestrations are included in both the sleeve and rod such that an axis, which is orthogonal to a long axis of the sleeve, traverse the apertures. Multiple apertures may be included in the rod and sleeve such that the apertures cooperate to provide a continuous void that extends from one side of the sleeve, across the rod, and through the other side of sleeve to provide a path for bone fusion/growth.

An alternative embodiment of the bone anchor system comprises: a sleeve (301) that includes: (a) a central sleeve channel (302) that traverses the sleeve and extends from a proximal end (303) of the sleeve to a distal end (304) of the sleeve, (b) first (305) and second (306) threaded portions on an outer surface of the sleeve, (c) a non-threaded portion (307) on the outer surface of the sleeve and existing between the first and second threaded portions, (d) a central sleeve axis (308) that extends from the proximal end of the sleeve to the distal end of the sleeve, and (e) a plurality of linear projections (309) on a wall of the central sleeve channel. The system includes a rod (310) that includes: (a) a central rod channel (311) that traverses the rod and extends from a proximal end of the rod to a distal end of the rod, (b) a head (312) on the proximal end of the rod, the head including a circular cross-section; (c) a central rod axis that extends from the proximal end of the rod to the distal end of the rod, and (e) a plurality of linear slots (313) on an outer surface of the rod.

In an embodiment, a first of the plurality of the linear projections includes a first projection long axis that is parallel to the central sleeve axis and a second of the plurality of linear projections includes a second projection long axis that is parallel to the central sleeve axis.

In an embodiment, a first of the plurality of the linear slots includes a first slot long axis that is parallel to the central rod axis; and a second of the plurality of linear slots includes a second slot long axis that is parallel to the central rod axis.

In an embodiment, the central sleeve channel includes first (314), second (315), and third (316) inner diameters. The first inner diameter is distal to the second and third inner diameters and the second inner diameter is between the first and third inner diameters. The second inner diameter is less than the third inner diameter. For example, diameter 314 may be less than diameter 315 as a result of forming slots in the rod. In other words, dimeter 314 is the same as the diameter of the rod taken from a slot to another slot on the opposing side of the rod.

In an embodiment the first inner diameter is less than the second inner diameter.

In an embodiment, the rod includes first, second, and third outer diameters. The first outer diameter is distal to the second and third outer diameters and the second outer diameter is between the first and third outer diameters. The second outer diameter is less than the third outer diameter.

Figure 3A:
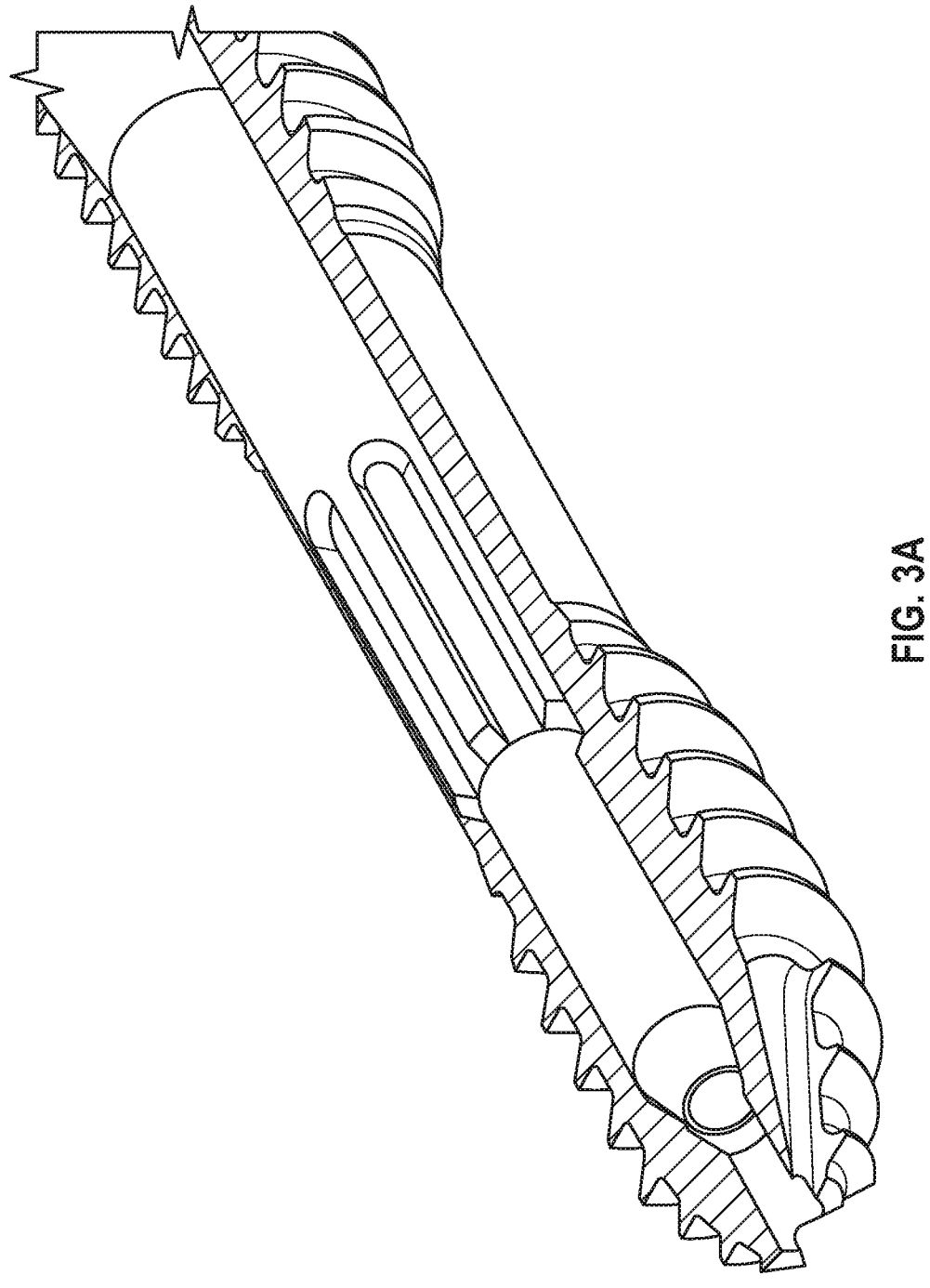
FIGS. 3A, 3B, 3C, 3D, 3E provide differing views of an
embodiment.
Figure 3B:
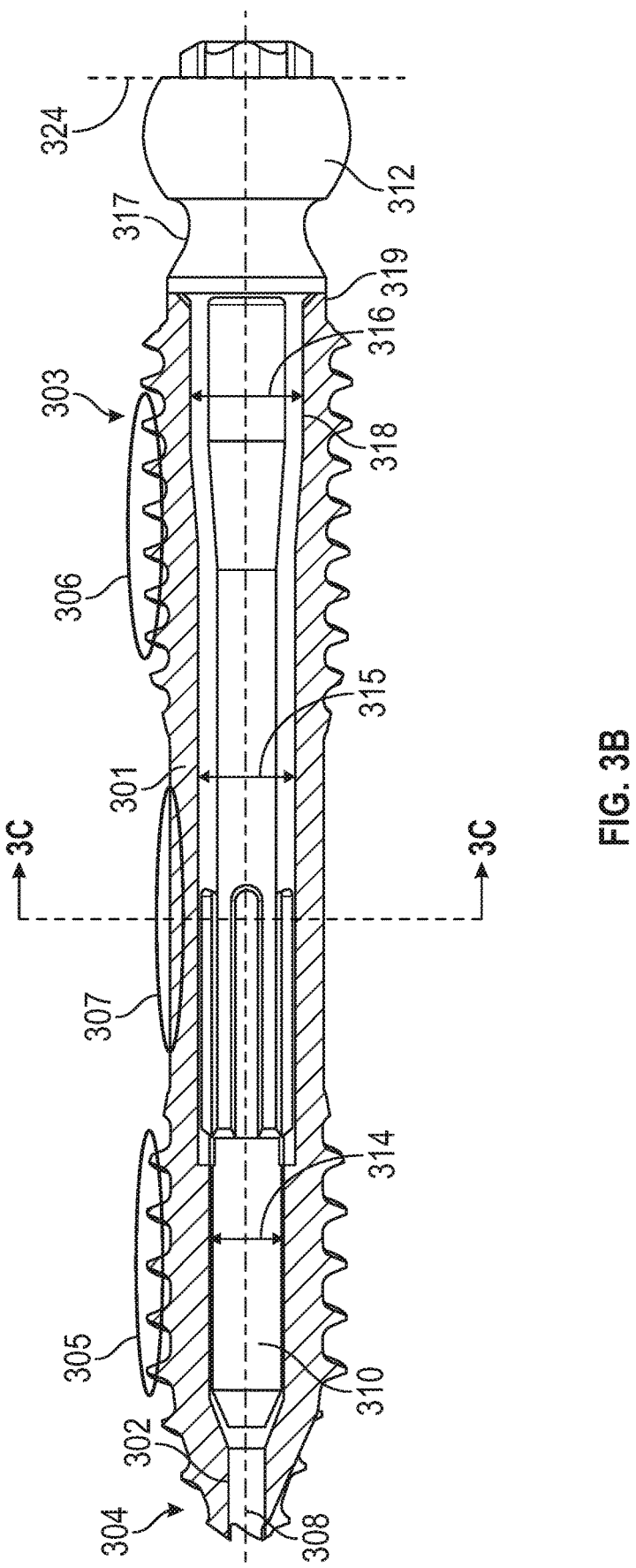
Figure 3C:
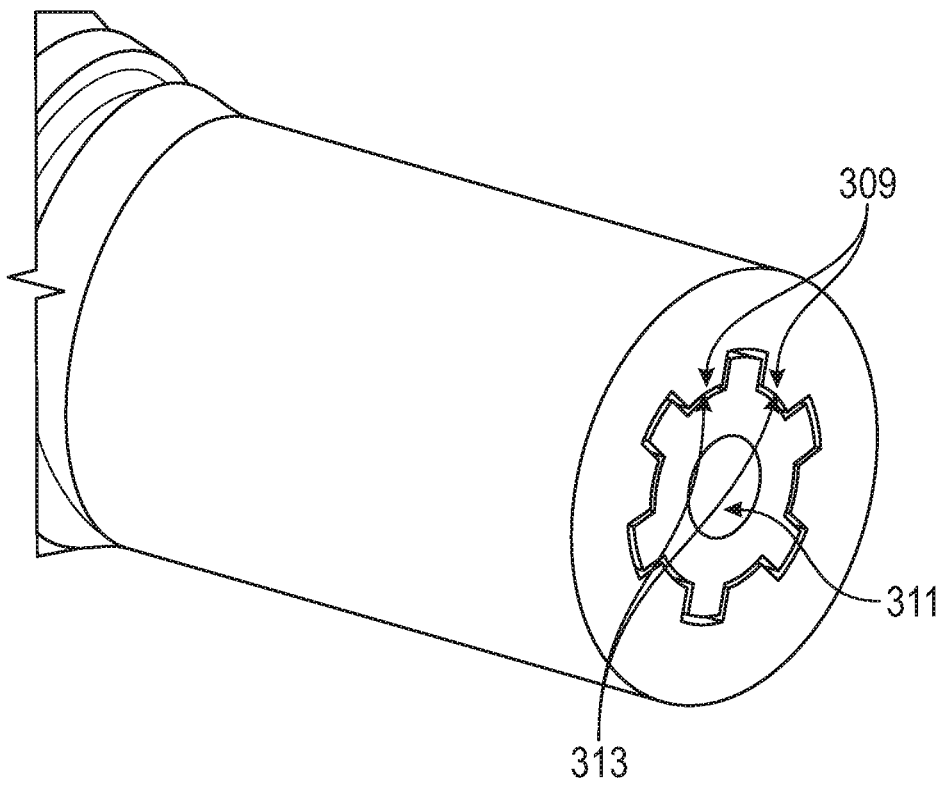
Figure 3D:
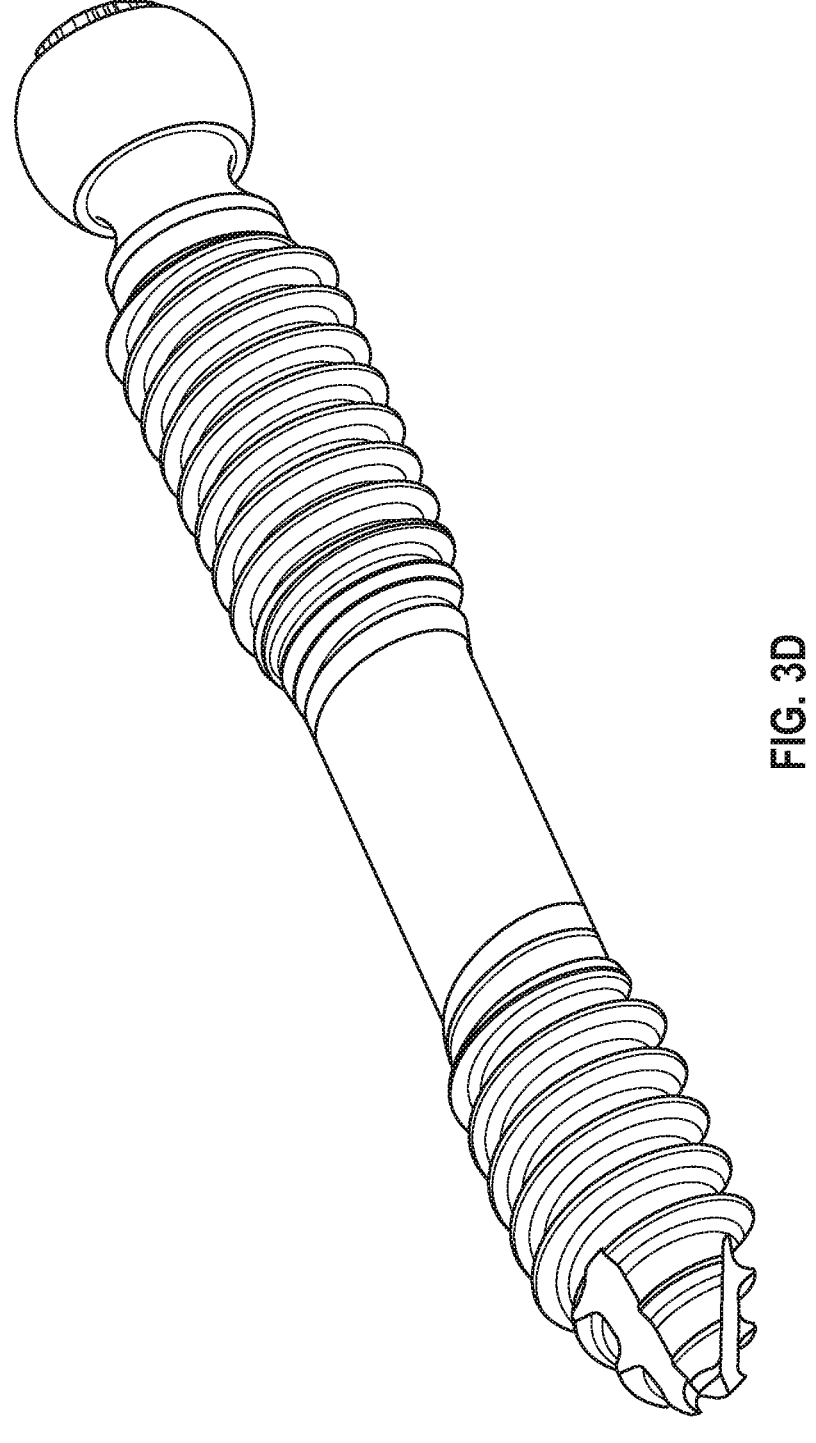
Figure 3E:
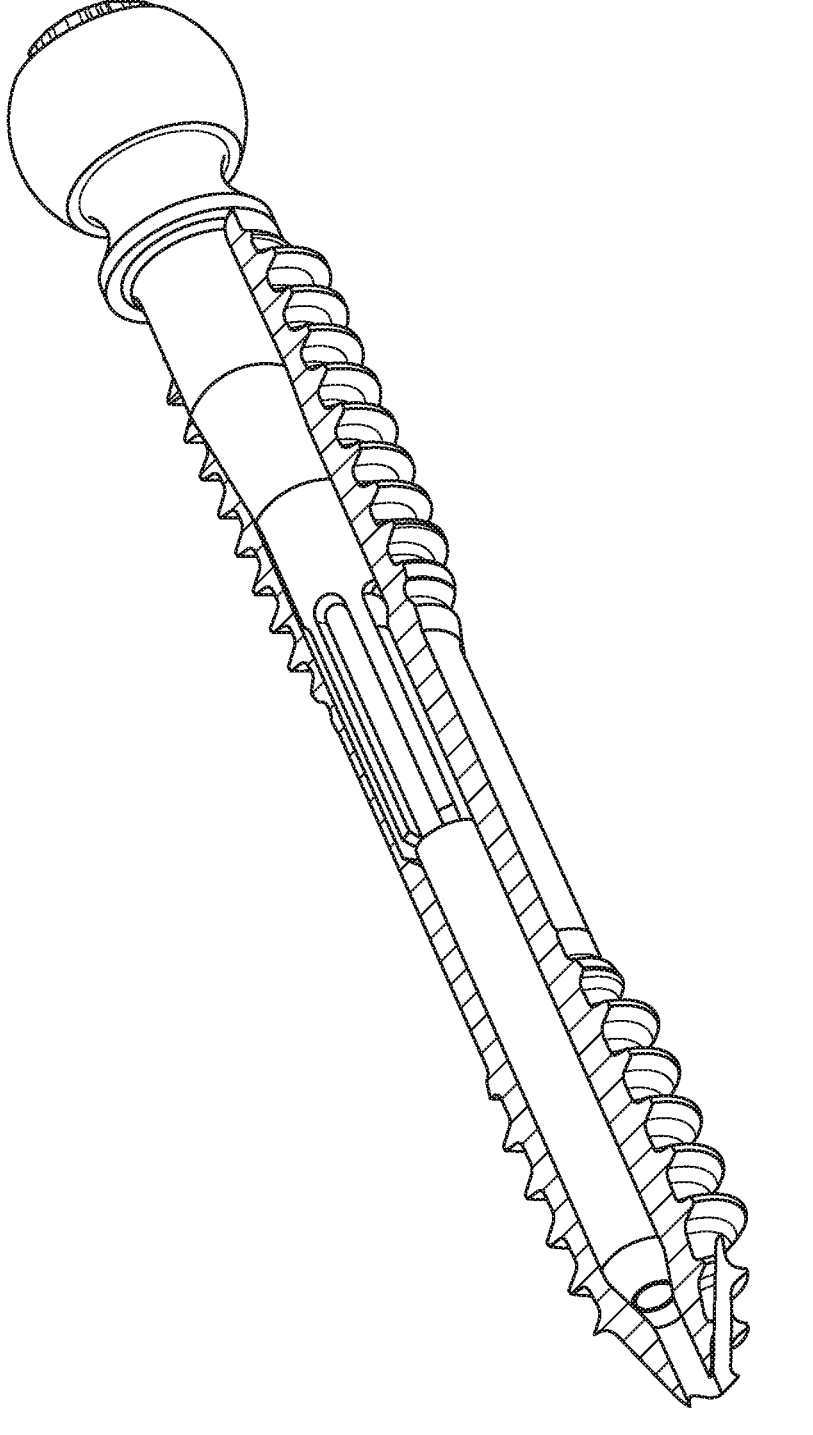
Figure 3F:
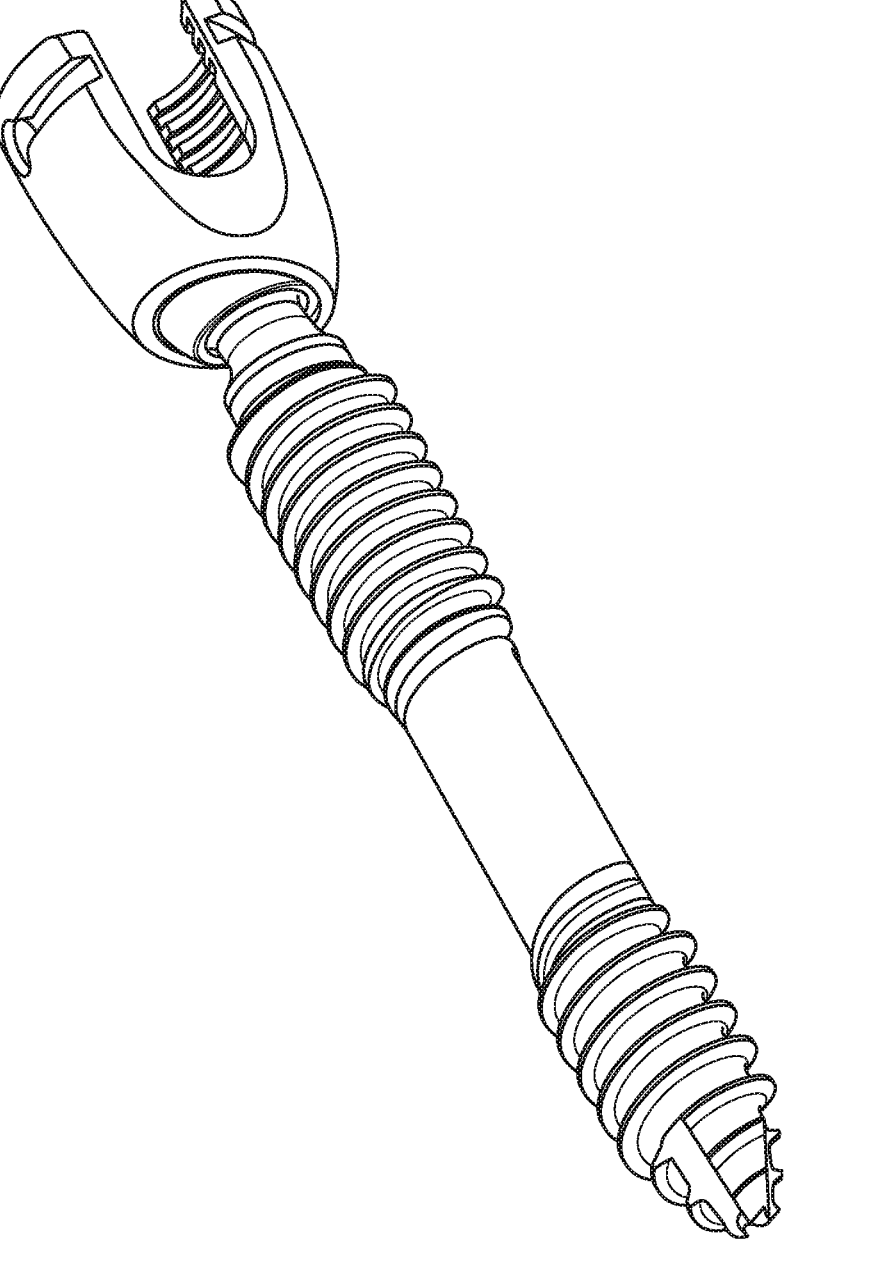
FIGS. 3F, 3G, 3H provide differing
views of the embodiment of FIG. 3B but with a tulip
attached to the head of the rod.
Figure 3G:
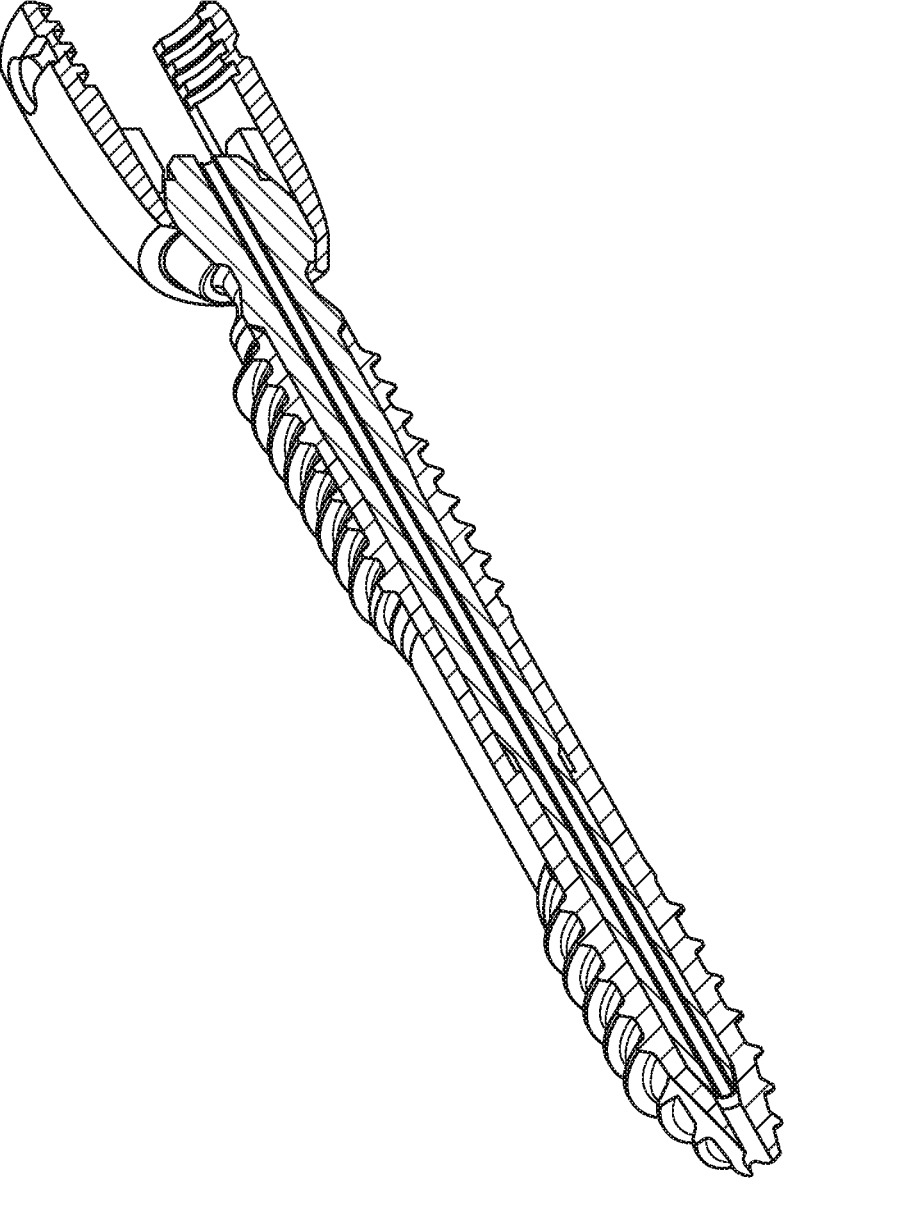
Figure 3H:
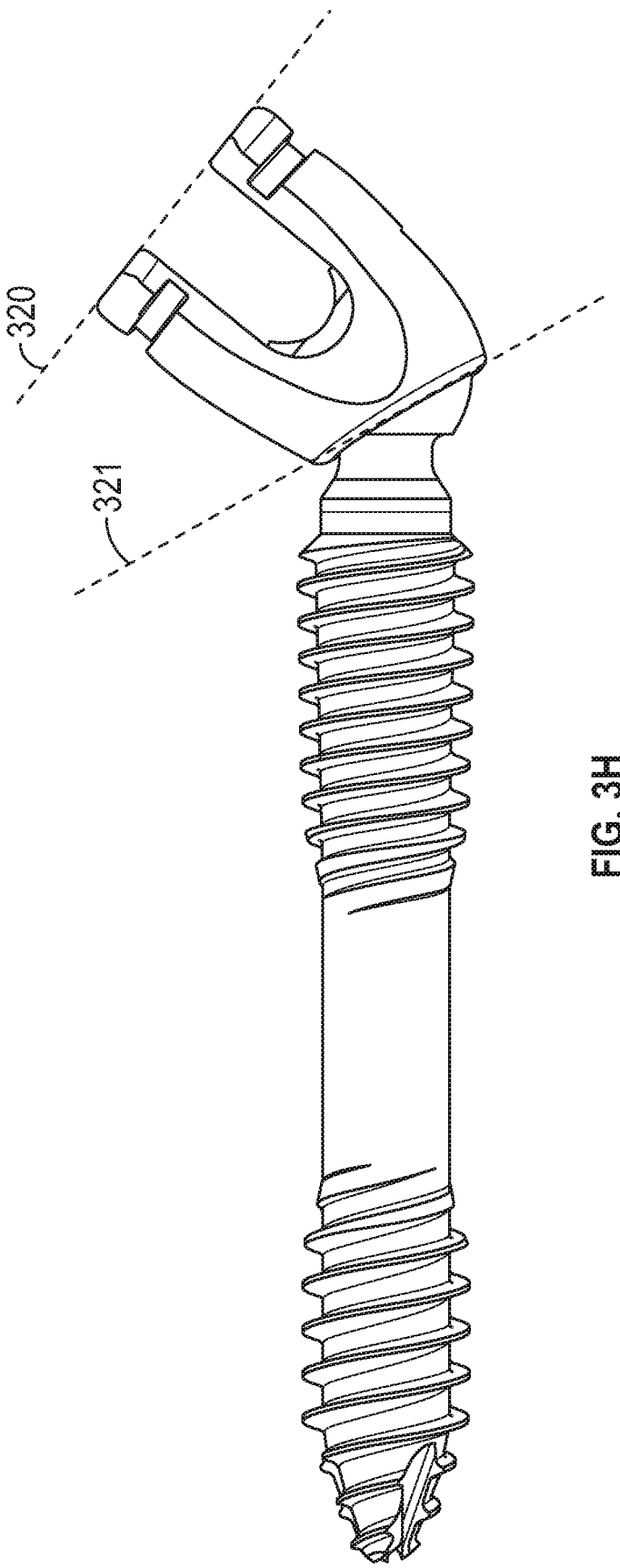

In an embodiment, the first outer diameter is less than the second outer diameter. However, in other embodiments the diameter relationships are not so limited and may include more or fewer distinct outer diameters for the rod. For example, diameter 1 (314) may remain but diameter 2 (315) may extend proximally to end 303. In an embodiment, inner diameters for the sleeve correspond to outer diameters for the rod. In other words, the inner and outer diameters generally match as shown in FIG. 3B.

In an embodiment, the rod tapers outwardly between the second and third outer diameters. This tapering may add strength to the rod and prevent failure under high torque situations (as opposed to sudden changes in diameter such as 90-degree changes). In an embodiment, at least a portion of the rod tapers outwardly as it extends proximally. In an embodiment, at least a portion of the sleeve tapers outwardly as it extends proximally.

In an embodiment, a least a portion of the plurality of linear slots are included in a proximal half of the rod. By locating the slots near head 312, any fouling of the slots may be more quickly remedied by a clinician or manufacturer. For example, any particulate matter in the male/female keying mechanism (i.e., slots and projections) may be more quickly removed the more proximal the keying mechanism. Further, the slot/projection keying may serve to prevent rotation of the rod within the sleeve during implantation while also avoiding the manufacturing nuances needed for thread formation and/or the risk of cross-threading or fouling the threads with un-intended particulate matter and the like.

Figure 5A:
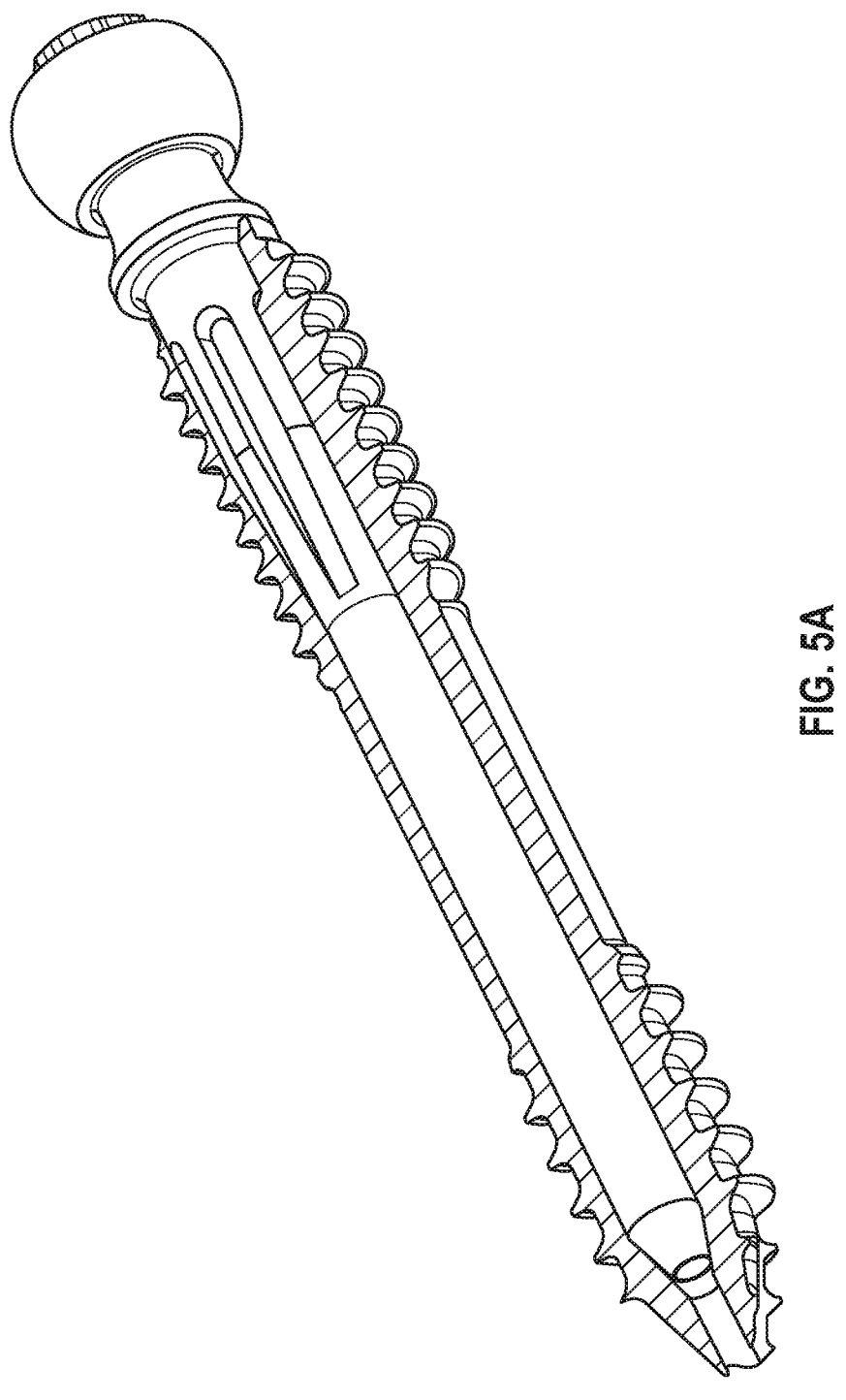
FIGS. 5A, 5B provide differing views of an embodiment.
Figure 5B:
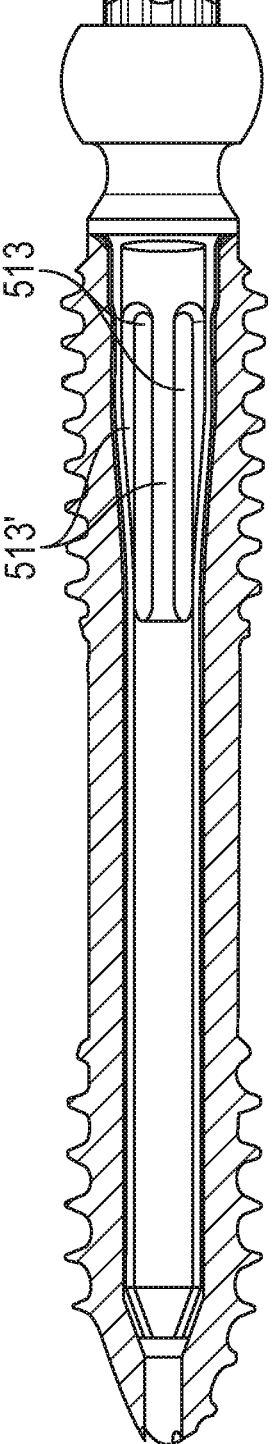

For example, FIGS. 5A, 5B include an embodiment with slots 513 and rod fins/male projections 513' in the proximal half of the rod. As seen in FIG. 5B, each of the rod and the sleeve may be interpreted as having both male/female keyed portions that correspond with one another to resist rotation of the rod with respect to the sleeve.

Figure 6A:
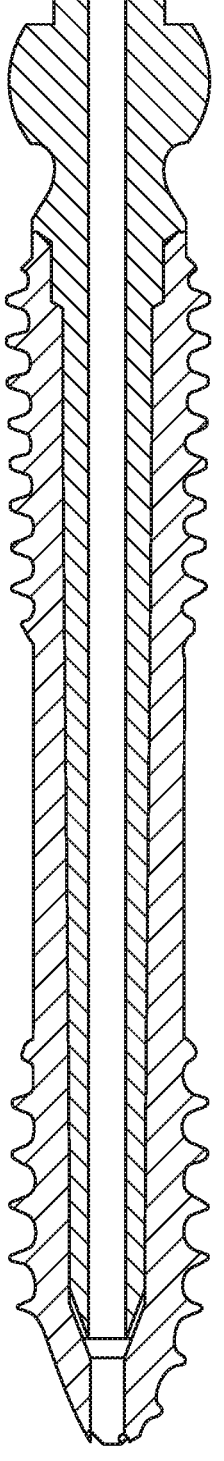
FIGS. 6A, 6B provide differing views of an embodiment.
Figure 6B:
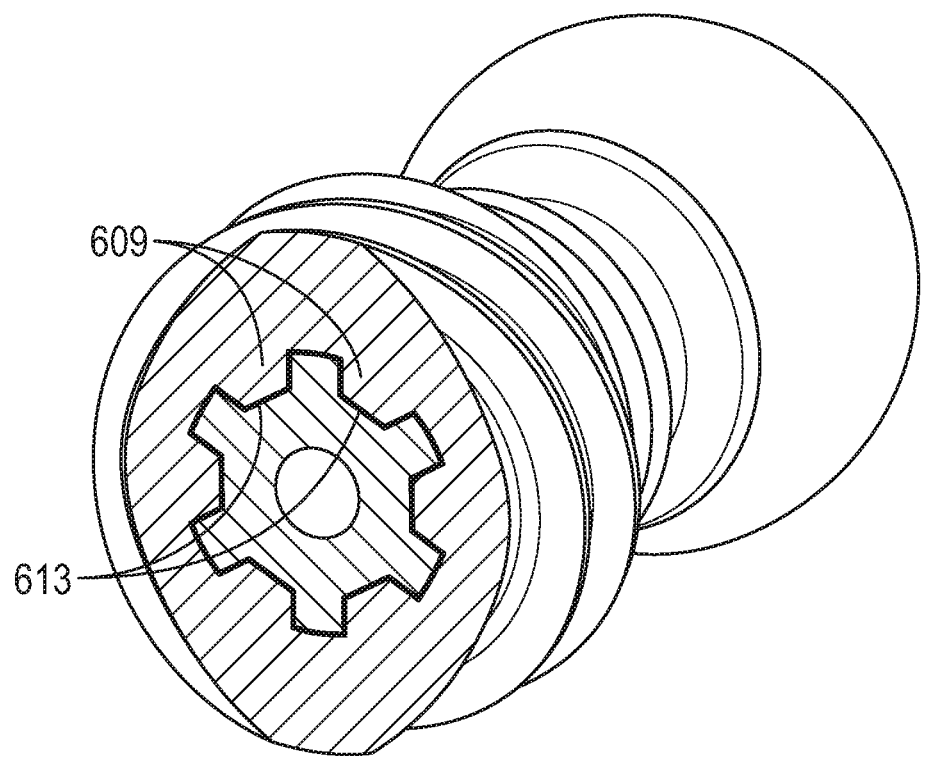

FIGS. 6A, 6B show an embodiment with more truncated keying elements located in the proximal half of the rod and sleeve. For example, see linear projections (609) on a wall of the central sleeve channel and linear slots 613 on an outer surface of the rod. This keyed arrangement is also present in the embodiment of FIG. 5A (although the structure of the sleeve inner wall is not as easily seen in that perspective).

An embodiment comprises a tulip configured to substantially surround the head of the rod. In an embodiment, the tulip includes a slot to slide around neck 317. However, in another embodiment the tulip may include resilient members which "pop" over head 312 and around neck 317. The tulip may be coupled to the head at a manufacturing facility and then shipped to a clinic or the tulip may be joined to the head by the clinician at the clinic.

Figure 4A:
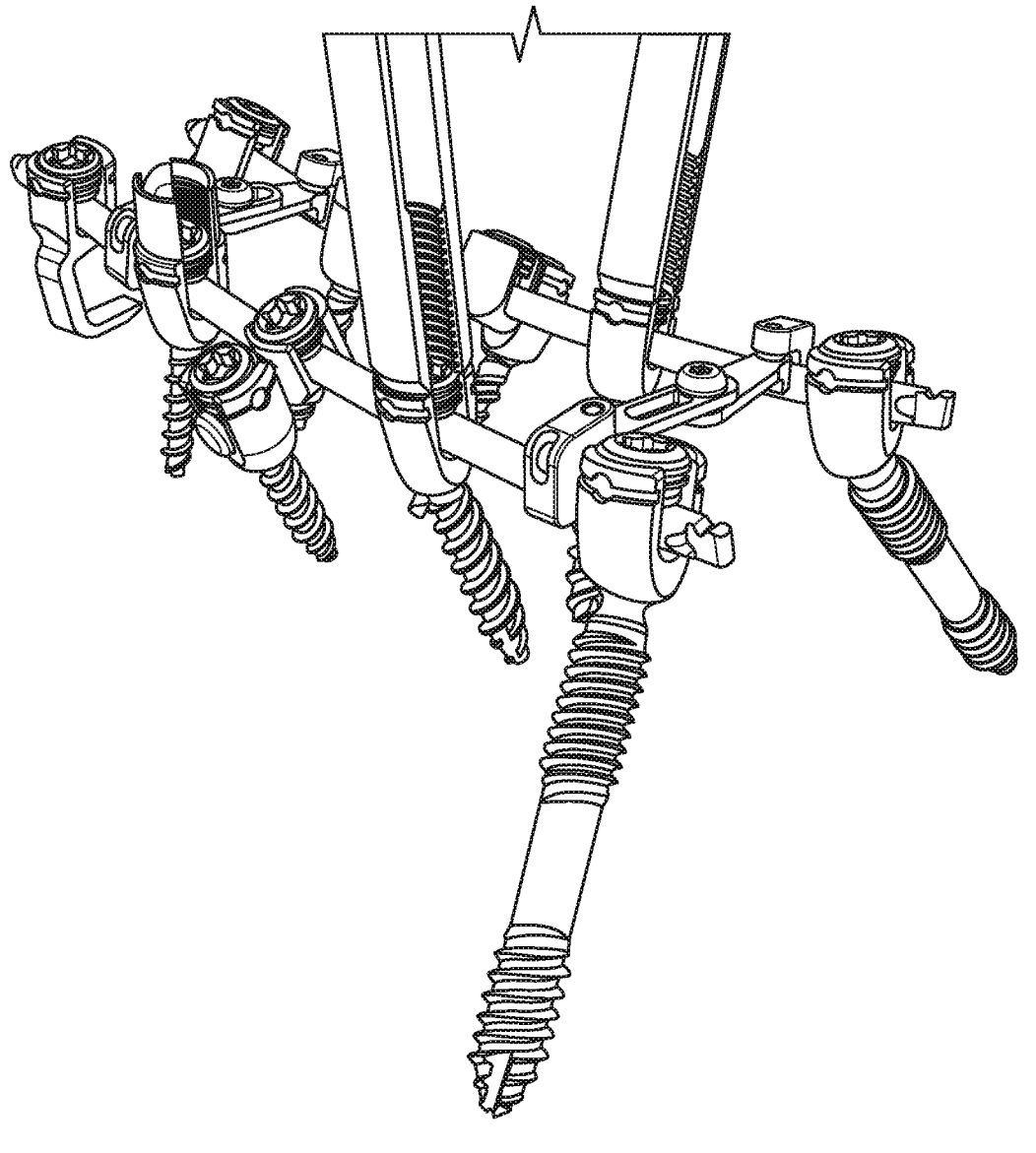
FIGS. 4A, 4B, 4C, 4D provide differing views of an
embodiment of the implant included within a fusion system
that extends from the SI joint to vertebral members.
Figure 4B:
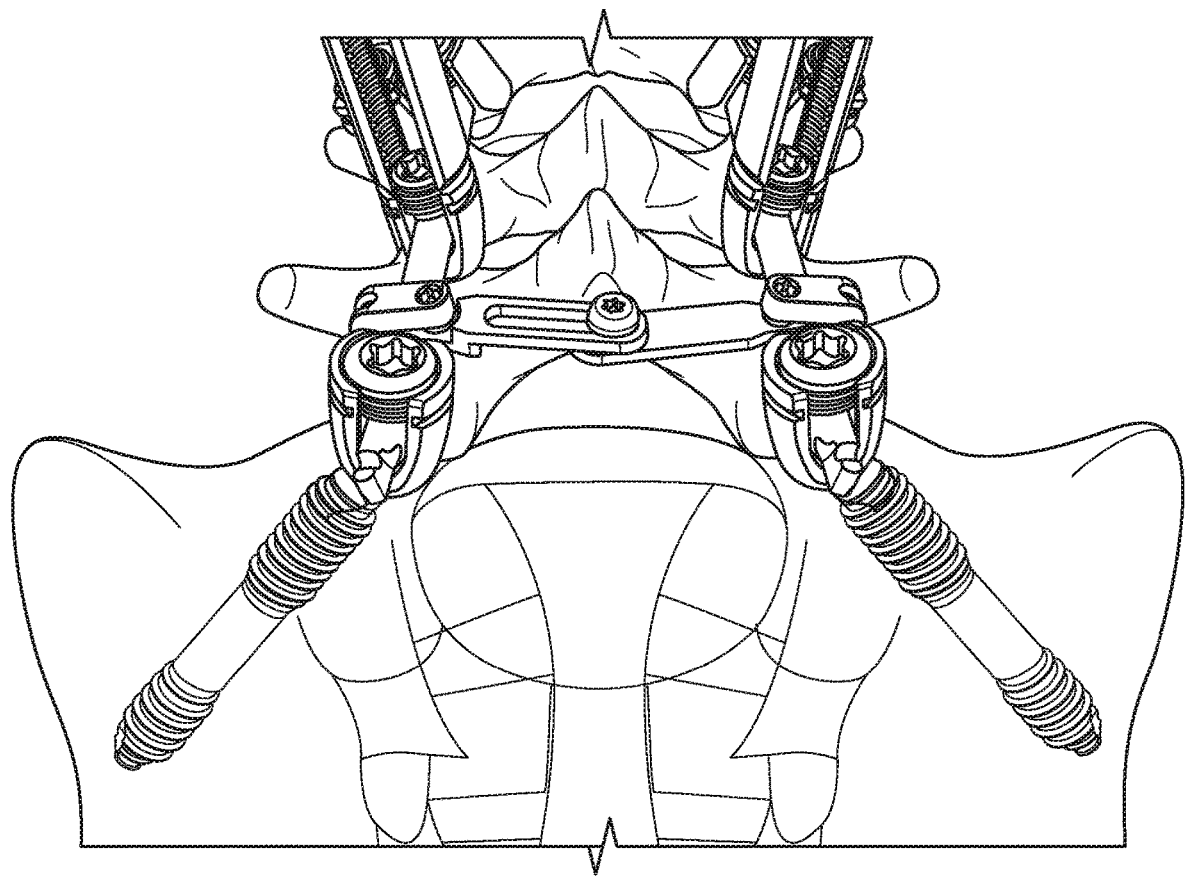
Figure 4C:
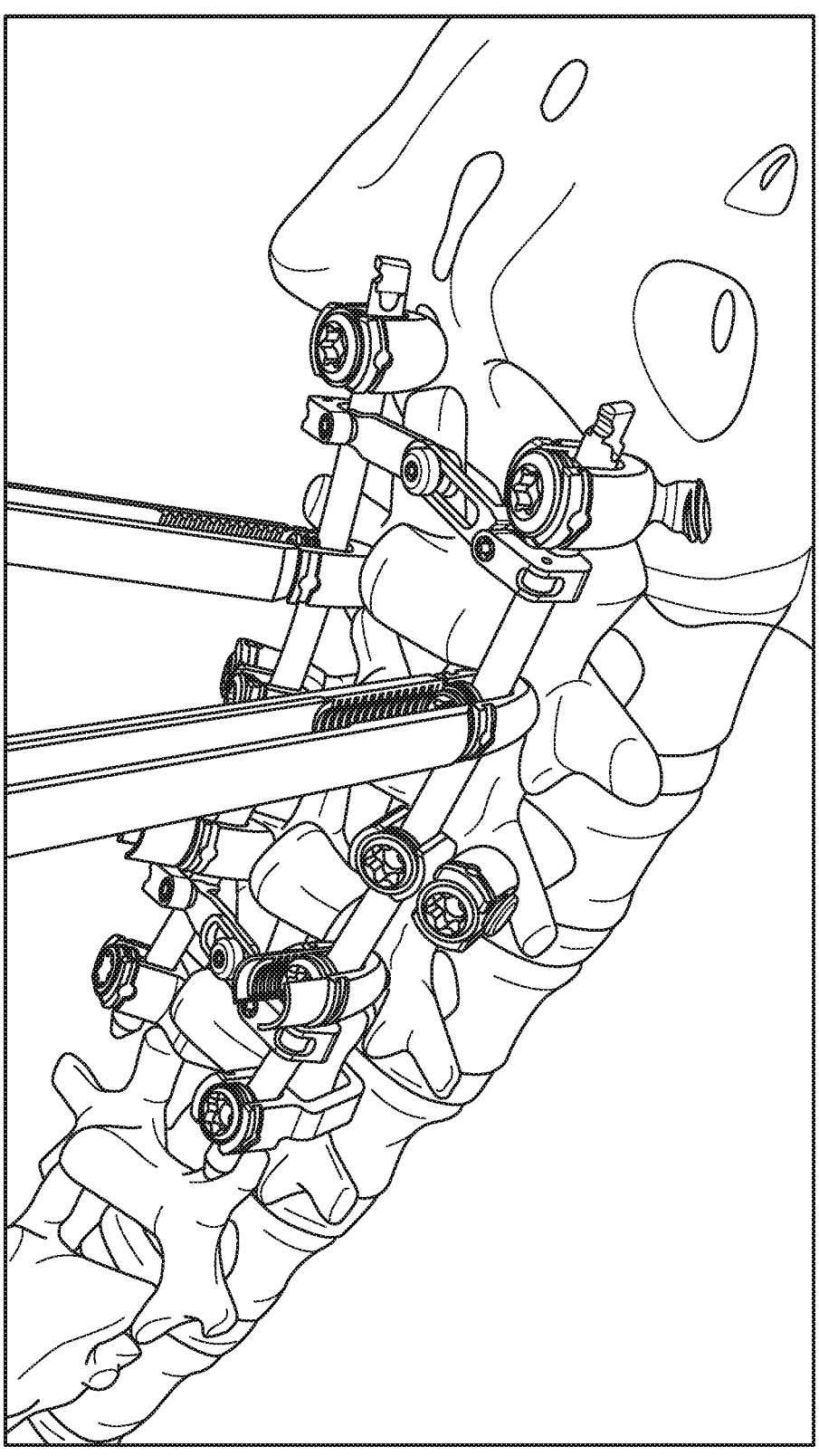
Figure 4D:
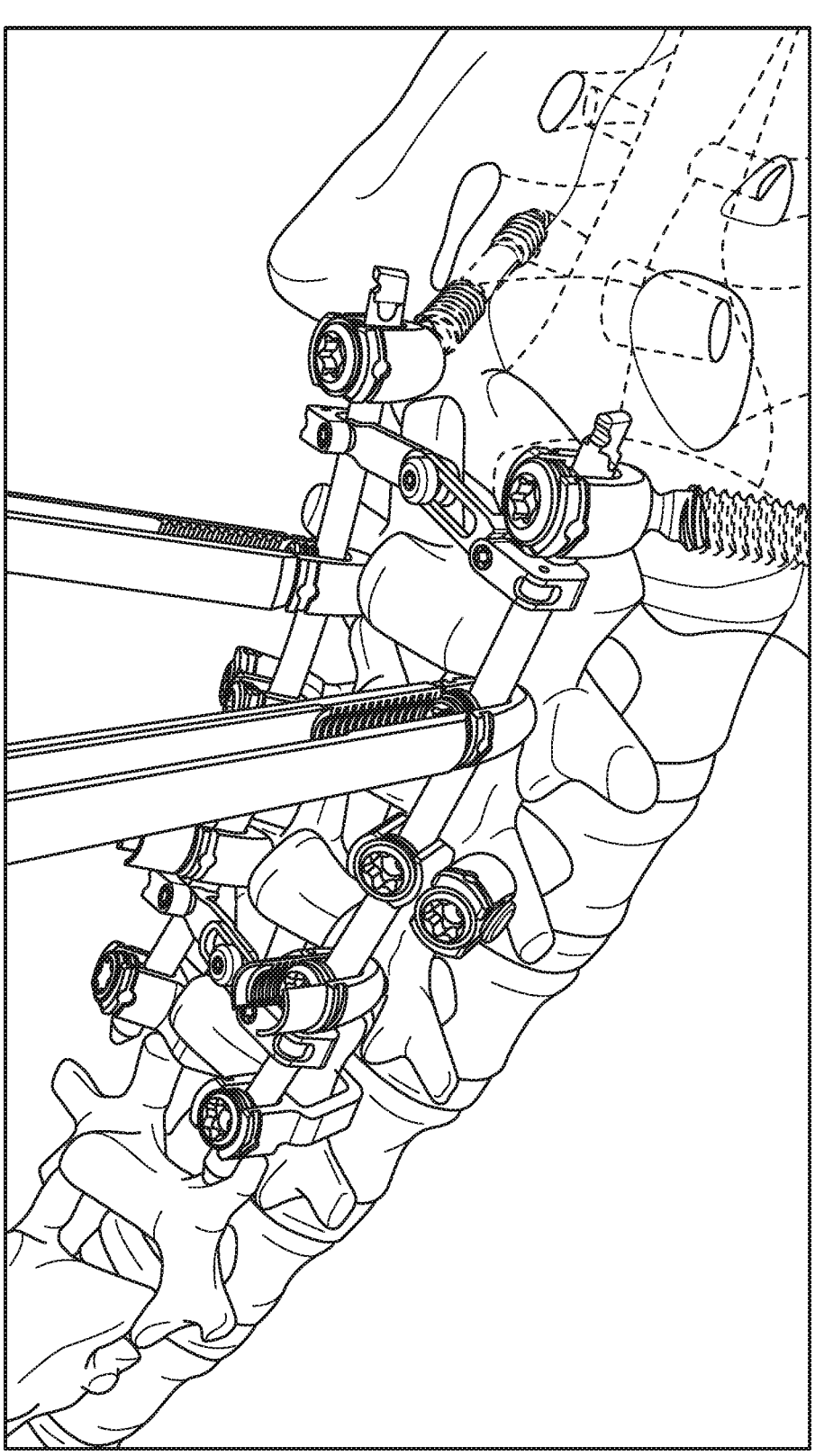

In an embodiment, the tulip may be used to couple the bone anchor system to a rod that affixes to additional tulips and bone anchors as shown in, for example, FIG. 4C. Such a system may promote better load distribution among the spine to increase the lifespan of the implants. In other words, the coupling of the SI anchor system to a vertebral anchor system may better distribute post-implant loading and lengthen the lifespan of the implant system and procedure.

In an embodiment the tulip includes a distal surface and a proximal surface. The proximal surface provides an opening to a trough, the through being configured to receive a fusion rod. The distal surface includes an aperture to encircle at least a portion of the head on the proximal end or the rod and/or a neck that couples the head of the rod to a main body of the rod. The proximal surface is coplanar with a first plane (320) and the distal surface is coplanar with a second plane (321). The first and second planes are not parallel with each other.

An embodiment includes a plurality of apertures that each couple the central sleeve channel to the outer surface of the sleeve. For an analogous aperture, see element 101 of FIG. 1A. For example, such an aperture may be included in region 307 to promote fusion along the SI joint. Region 307 is configured to be located at the SI joint in embodiments of some surgical techniques. In an embodiment, the plurality of apertures includes a first aperture and a second aperture. The first aperture includes a long axis parallel to the central sleeve axis. The first aperture includes a short axis orthogonal to the long axis of the first aperture. The first aperture includes a length measured along the long axis of the first aperture and a width measured along the short axis of the first aperture. The length of the first aperture is greater than the width of the first aperture.

In an embodiment, the sleeve is a sacroiliac bone anchor.

In an embodiment the first threaded portion includes a first thread pitch for a majority of threads of the first threaded portion. The second threaded portion includes a second thread pitch for a majority of threads of the second threaded portion. The first thread pitch is unequal to the second thread pitch. As used herein, thread pitch is measured from the peak of one thread to the peak of an immediately adjacent thread. In an embodiment, the first thread pitch is larger than the second thread pitch and the first threaded portion is distal to the second threaded portion.

In an embodiment, the outer sleeve is a compression screw. As used herein, a compression screw compresses two articles against one another when the screw is drilled across a seam that exists between the two articles. For example, differing thread pitches for areas 305, 306 result in a compression or lag screw that draws bone portions on either side of the SI joint towards each other in compression (i.e., one set of threads moves more quickly than another set of threads resulting in compression of adjacent bone portions). Smooth area 307 is configured to span the SI joint upon final implantation and its smoothness allows bone portions on either side of the SI joint to move/slide as fusion occurs over time.

In an embodiment, the bone anchor is a sacroiliac joint screw.

In an embodiment, the sleeve is a non-milled conduit and the rod is a milled conduit. However, in another embodiment the sleeve is a printed conduit.

In an embodiment, the sleeve includes projections on the outer surface of the sleeve and the projections are monolithic with the sleeve. As used herein, "monolithic" means formed from a single piece without use of adhesives, welds, or other coupling agents or means.

In an embodiment, the sleeve is welded to the rod. For example, at least one weld may be located at one or both of locations 318 (made via a hole formed in threads 306), 319 (at the most proximal sleeve/rod junction).

In an embodiment, the sleeve is permanently and non-slidingly coupled to the rod. For example, in an embodiment the sleeve is manufactured via a 3D printing process whereas the rod is manufactured via, for example, milling. As a result, the rod may have a higher strength with which to better tolerate torque and other forces experienced during implantation of the device and/or forces generated by the patient long after implantation. For example, high torque forces may be experienced at neck 317 during implantation of the system. However, the 3D process may allow for biocompatible surfaces that promote bone growth and better coupling between the implant and bone. For example, the surface of the sleeve may include irregular finger-like projections that are printed along with the rest of the sleeve with the projections and main conduit of the sleeve being monolithic with each other. Such projections may not be possible to form via a process such as milling.

In an embodiment, the sleeve is manufactured via additive manufacturing (e.g., 3D printing) while the rod is formed via milling. Then, at the manufacturing facility, the rod is forced into the sleeve and is retained within the sleeve via a resistance fit. In an embodiment, the rod is actually compressed radially by the sleeve. Further, the male/female locking portions 309, 313 resist rotation of the rod within the sleeve during, for example, insertion of the implant into the patient. The system may be shipped to a clinical facility with the rod already inserted into the sleeve. In fact, in an embodiment the sleeve and rod are permanently coupled to each other via at least one weld. The clinician may then receive the already coupled sleeve and rod from a sterile package and proceed to implant the sleeve and rod simultaneously. As a result, the benefits of additive manufacturing (e.g., biocompatible surface) are delivered along with the benefits of more robust manufacturing (e.g., milled rod) that has strength to tolerate high torque forced experienced during implantation.

In an embodiment, the central rod axis is coaxial with the central sleeve axis.

In an embodiment, the head of the rod includes a proximal face; the rod includes a projection that projects proximally from the proximal face; the projection is configured to couple to an anchor driver. In an embodiment, the projection includes a side wall that extends proximally from the proximal face and parallel to the central rod axis; the proximal face is coplanar with third plane (324); and the side wall is orthogonal to the third plane. Such an arrangement of the proximal face and projection helps eliminate or lessen "screw toggle" where a screw or anchor is not rigidly affixed to a driver (e.g., screw driver) and therefore may include a long axis that is not collinear with a long axis of the driver. Screw toggle can be frustrating for clinicians trying to drive screws into bone a precise angle.

In an embodiment, the sleeve includes titanium and the rod includes titanium.

Further examples follow. For illustrative purposes, an Example X+1 in Example Set A referring to Example X is referring to Example X from Example Set A and not Example Set B or some other example set.

Example Set A

Example 1. A bone anchor system comprising: a sleeve (301) that includes: (a) a central sleeve channel (302) that traverses the sleeve and extends from a proximal end (303) of the sleeve to a distal end (304) of the sleeve, (b) first (305) and second (306) threaded portions on an outer surface of the sleeve, (c) a non-threaded portion (307) on the outer surface of the sleeve and existing between the first and second threaded portions, (d) a central sleeve axis (308) that extends from the proximal end of the sleeve to the distal end of the sleeve, and (e) a plurality of linear projections (309) on a wall of the central sleeve channel; a rod (310) that includes: (a) a central rod channel (311) that traverses the rod and extends from a proximal end of the rod to a distal end of the rod, (b) a head (312) on the proximal end of the rod, the head including a circular cross-section; (c) a central rod axis that extends from the proximal end of the rod to the distal end of the rod, and (e) a plurality of linear slots (313) on an outer surface of the rod; wherein: (a) the rod is proportioned to slide within the central sleeve channel, and (b) the plurality of linear projections is proportioned to slide within the plurality of linear slots.

Alternative version of Example 1. A bone anchor system comprising: a sleeve (301) that includes: (a) a central sleeve channel (302) that traverses the sleeve and extends from a proximal end (303) of the sleeve to a distal end (304) of the sleeve, (b) first (305) and second (306) threaded portions on an outer surface of the sleeve, (c) a central sleeve axis (308) that extends from the proximal end of the sleeve to the distal end of the sleeve, and (e) a plurality of linear projections (309) on a wall of the central sleeve channel; a rod (310) that includes: (a) a central rod channel (311) that traverses the rod and extends from a proximal end of the rod to a distal end of the rod, (b) a head (312) on the proximal end of the rod, the head including a circular cross-section; (c) a central rod axis that extends from the proximal end of the rod to the distal end of the rod, and (e) a plurality of linear slots (313) on an outer surface of the rod; wherein: (a) the rod is proportioned to slide within the central sleeve channel, and (b) the plurality of linear projections is proportioned to slide within the plurality of linear slots.

Alternative version of Example 1. A bone anchor system comprising: a sleeve (301) that includes: (a) a central sleeve channel (302) that traverses the sleeve and extends from a proximal end (303) of the sleeve to a distal end (304) of the sleeve, (b) first (305) and second (306) threaded portions on an outer surface of the sleeve, (c) a non-threaded portion (307) on the outer surface of the sleeve and existing between the first and second threaded portions, (d) a central sleeve axis (308) that extends from the proximal end of the sleeve to the distal end of the sleeve, and (e) a plurality of linear projections (309) on a wall of the central sleeve channel; a rod (310) that includes: (a) a central rod channel (311) that traverses the rod and extends from a proximal end of the rod to a distal end of the rod, (b) a head (312) on the proximal end of the rod, the head including a circular cross-section; (c) a central rod axis that extends from the proximal end of the rod to the distal end of the rod, and (e) a plurality of linear slots (313) on an outer surface of the rod.

Example 2. The system of Example 1, wherein: a first of the plurality of the linear projections includes a first projection long axis that is parallel to the central sleeve axis; a second of the plurality of linear projections includes a second projection long axis that is parallel to the central sleeve axis.

Example 3. The system of Example 2, wherein: a first of the plurality of the linear slots includes a first slot long axis that is parallel to the central rod axis; a second of the plurality of linear slots includes a second slot long axis that is parallel to the central rod axis.

Example 4. The system according to any of Examples 1-3, wherein: the central sleeve channel includes first (314), second (315), and third (316) inner diameters; the first inner diameter is distal to the second and third inner diameters and the second inner diameter is between the first and third inner diameters; the second inner diameter is less than the third inner diameter.

Example 5. The system of Example 4, wherein the first inner diameter is less than the second inner diameter.

Example 6. The system according to any of Examples 1-5, wherein: the rod includes first, second, and third outer diameters; the first outer diameter is distal to the second and third outer diameters and the second outer diameter is between the first and third outer diameters; the second outer diameter is less than the third outer diameter.

Example 7. The system of Example 6, wherein the first outer diameter is less than the second outer diameter.

Example 7.1 The system according to any of Examples 6 to 7, wherein the rod tapers outwardly between the second and third outer diameters.

Example 8. The system according to any of Examples 1 to 7, wherein the a least a portion of the plurality of linear slots are included in a proximal half of the rod.

Example 9. The system according to any of Examples 1 to 8 comprising a tulip configured to substantially surround the head of the rod.

Example 9.1 The system of Example 9, wherein: the tulip includes a distal surface and a proximal surface; the proximal surface provides an opening to a trough, the through being configured to receive a fusion rod; the distal surface includes an aperture to encircle at least a portion of the head on the proximal end, a neck that couple the head of the rod to a main body of the rod; the proximal surface is coplanar with a first plane (320) and the distal surface is coplanar with a second plane (321); the first and second planes are not parallel with each other.

Example 10. The system according to any of Examples 1 to 9 comprising a plurality of apertures that each couple the central sleeve channel to the outer surface of the sleeve, Example 11. The system according to any of Examples 1-10, wherein: the plurality of apertures includes a first aperture and a second aperture; the first aperture includes a long axis parallel to the central sleeve axis; the first aperture includes a short axis orthogonal to the long axis of the first aperture; the first aperture includes a length measured along the long axis of the first aperture and a width measured along the short axis of the first aperture; the length of the first aperture is greater than the width of the first aperture.

Example 12. The system according to any of Examples 1 to 11, wherein the sleeve is a sacroiliac bone anchor.

Example 13. The system according to any of Examples 1 to 12, wherein: the first threaded portion includes a first thread pitch for a majority of threads of the first threaded portion; the second threaded portion includes a second thread pitch for a majority of threads of the second threaded portion; the first thread pitch is unequal to the second thread pitch.

Example 14. The system of Example 13, wherein: the first thread pitch is larger than the second thread pitch; the first threaded portion is distal to the second threaded portion.

Example 15. The system of Example 14, wherein the outer sleeve is a compression screw.

Example 15.1 The system according to any of Examples 1 to 15, wherein the bone anchor is a sacroiliac joint screw.

Example 16. The system according to any of Examples 1 to 15, wherein: the sleeve is a non-milled conduit; the rod is a milled conduit.

Example 17. The system according to any of Examples 1 to 16, wherein the sleeve is a printed conduit.

Example 18. The system according to any of Examples 1 to 17, wherein: the sleeve includes projections on the outer surface of the sleeve; the projections are monolithic with the sleeve.

Example 19. The system according to any of Examples 1 to 18, wherein the sleeve is welded to the rod.

Example 20. The system according to any of Examples 1 to 18, wherein the sleeve is permanently and non-slidingly coupled to the rod.

Example 21. The system according to any of Examples 1 to 20, wherein the central rod axis is coaxial with the central sleeve axis.

Example 22. The system according to any of Examples 1 to 21, wherein; the head of the rod includes a proximal face; the rod includes a projection that projects proximally from the proximal face; the projection is configured to couple to an anchor driver.

Example 23. The system of Example 22, wherein: the projection includes a side wall that extends proximally from the proximal face and parallel to the central rod axis; the proximal face is coplanar with third plane (324); the side wall is orthogonal to the third plane.

Example 24. The system according to any of Examples 1 to 23, wherein: the sleeve includes titanium; the rod includes titanium.

Example 25. A bone anchor system comprising: a first conduit that includes: (a) a central first conduit channel that traverses the first conduit and extends from a proximal end of the first conduit to a distal end of the first conduit, (b) first and second threaded portions on an outer surface of the first conduit, (c) a non-threaded portion on the outer surface of the first conduit and existing between the first and second threaded portions, (d) a central first conduit axis that extends from the proximal end of the first conduit to the distal end of the first conduit, and (e) a first keyed element on a wall of the central first conduit channel; a second conduit that includes: (a) a central second conduit channel that traverses the second conduit and extends from a proximal end of the second conduit to a distal end of the second conduit, (b) a head on the proximal end of the second conduit, the head including a circular cross-section; (c) a central second conduit axis that extends from the proximal end of the second conduit to the distal end of the second conduit, and (e) a second keyed element on an outer surface of the rod; wherein second key element is complementary with the first keyed element.

Example Set B

Example 1. A bone anchor system comprising: a sleeve (701) that includes: (a) a central sleeve channel (702) that traverses the sleeve and extends from a proximal end (703) of the sleeve to a distal end (704) of the sleeve, (b) a threaded first portion (705) and a threaded second portion (706) on an outer surface of the sleeve, (c) a third portion (707) on the outer surface of the sleeve and existing between the first and second portions, (d) a central sleeve axis (708) that extends from the proximal end of the sleeve to the distal end of the sleeve, and (e) a plurality of threads (709) on a wall of the central sleeve channel; a rod (710) that includes: (a) a central rod channel (711) that traverses the rod and extends from a proximal end of the rod to a distal end of the rod, (b) a head (712) on the proximal end of the rod, the head including a circular cross-section; (c) a central rod axis that extends from the proximal end of the rod to the distal end of the rod, and (e) a plurality of threads (713) on an outer surface of the rod; wherein: (a) the rod is proportioned to slide within the central sleeve channel, and (b) the plurality of threads on the wall of the central sleeve channel.

Alternative version of Example 1. A bone anchor system comprising: a sleeve (701) that includes: (a) a central sleeve channel (702) that traverses the sleeve and extends from a proximal end (703) of the sleeve to a distal end (704) of the sleeve, (b) threaded first (705) and second (706) portions on an outer surface of the sleeve, (c) a central sleeve axis (708) that extends from the proximal end of the sleeve to the distal end of the sleeve, and (e) a plurality of threads (709) on a wall of the central sleeve channel; a rod (710) that includes: (a) a central rod channel (711) that traverses the rod and extends from a proximal end of the rod to a distal end of the rod, (b) a head (712) on the proximal end of the rod, the head including a circular cross-section; (c) a central rod axis that extends from the proximal end of the rod to the distal end of the rod, and (e) a plurality of threads (713) on an outer surface of the rod; wherein: (a) the rod is proportioned to slide within the central sleeve channel, and (b) the plurality of threads on the outer surface of the rod are configured to screw into the plurality of threads on the wall of the central sleeve channel.

For example, some embodiments may extend threads 705 or 706 into areas 707. Other embodiments may include a set of threads at area 707 with a pitch that differs from the pitch of threads of either or both of threads 705, 706. Fenestrations (i.e., apertures, holes) (751, 752) may be included in smooth or threaded areas of the sleeve and/or rod. In some embodiments, fenestrations are included in the sleeve but not the rod such that an axis (753, 753'), which is orthogonal to a long axis of the sleeve, traverses the aperture but not the rod (because the rod does not extend distally to the point of the aperture) to provide a path for bone fusion/growth.

Alternative version of Example 1. A bone anchor system comprising: a sleeve (701) that includes: (a) a central sleeve channel (702) that traverses the sleeve and extends from a proximal end (703) of the sleeve to a distal end (704) of the sleeve, (b) threaded first (705) and second (706) portions on an outer surface of the sleeve, (c) a central sleeve axis (708) that extends from the proximal end of the sleeve to the distal end of the sleeve, and (e) a plurality of threads (709) on a wall of the central sleeve channel; a rod (710) that includes: (a) a central rod channel (711) that traverses the rod and extends from a proximal end of the rod to a distal end of the rod, (b) a head (712) on the proximal end of the rod, the head including a circular cross-section; (c) a central rod axis that extends from the proximal end of the rod to the distal end of the rod, and (e) a plurality of threads (713) on an outer surface of the rod.

Example 2. The system of Example 1, wherein: the sleeve includes first (751) and second (752) apertures in a sidewall of the sleeve; an axis (753), which is orthogonal to the long axis of the sleeve, traverses the first and second apertures but not the rod.

For example, such an aperture may be included in region 707 to promote fusion along the SI joint. Region 707 is configured to be located at the SI joint in embodiments of some surgical techniques. In an embodiment, the first and second apertures are in a middle third of the sleeve. This positioning helps position the apertures across, for example, a fracture between two bone pieces and allow for fusion between the two bone pieces.

Example 3. The system of Example 1, wherein: the sleeve includes first and second apertures in a sidewall of the sleeve; the first aperture includes a long axis (754) parallel to the central sleeve axis; the first aperture includes a short axis orthogonal to the long axis of the first aperture; the first aperture includes a length measured along the long axis of the first aperture and a width measured along the short axis of the first aperture; the length of the first aperture is greater than the width of the first aperture.

Example 4. The system according to any of Examples 1-3, wherein: the central sleeve channel includes first (714), second (715), and third (716) inner diameters; the first inner diameter is distal to the second and third inner diameters and the second inner diameter is between the first and third inner diameters; the second inner diameter is less than the third inner diameter.

Example 5. The system of Example 4, wherein the first inner diameter is less than the second inner diameter.

Example 6. The system according to any of Examples 4-5, wherein a portion (760) of the central sleeve channel tapers outwardly as it extends proximally.

Example 7. The system of Example 6, wherein: a portion of the rod tapers outwardly as it extends proximally; a transverse axis is orthogonal to the central sleeve axis and intersects both the portion (760) of the central sleeve and the portion of the rod.

Figure 7A:
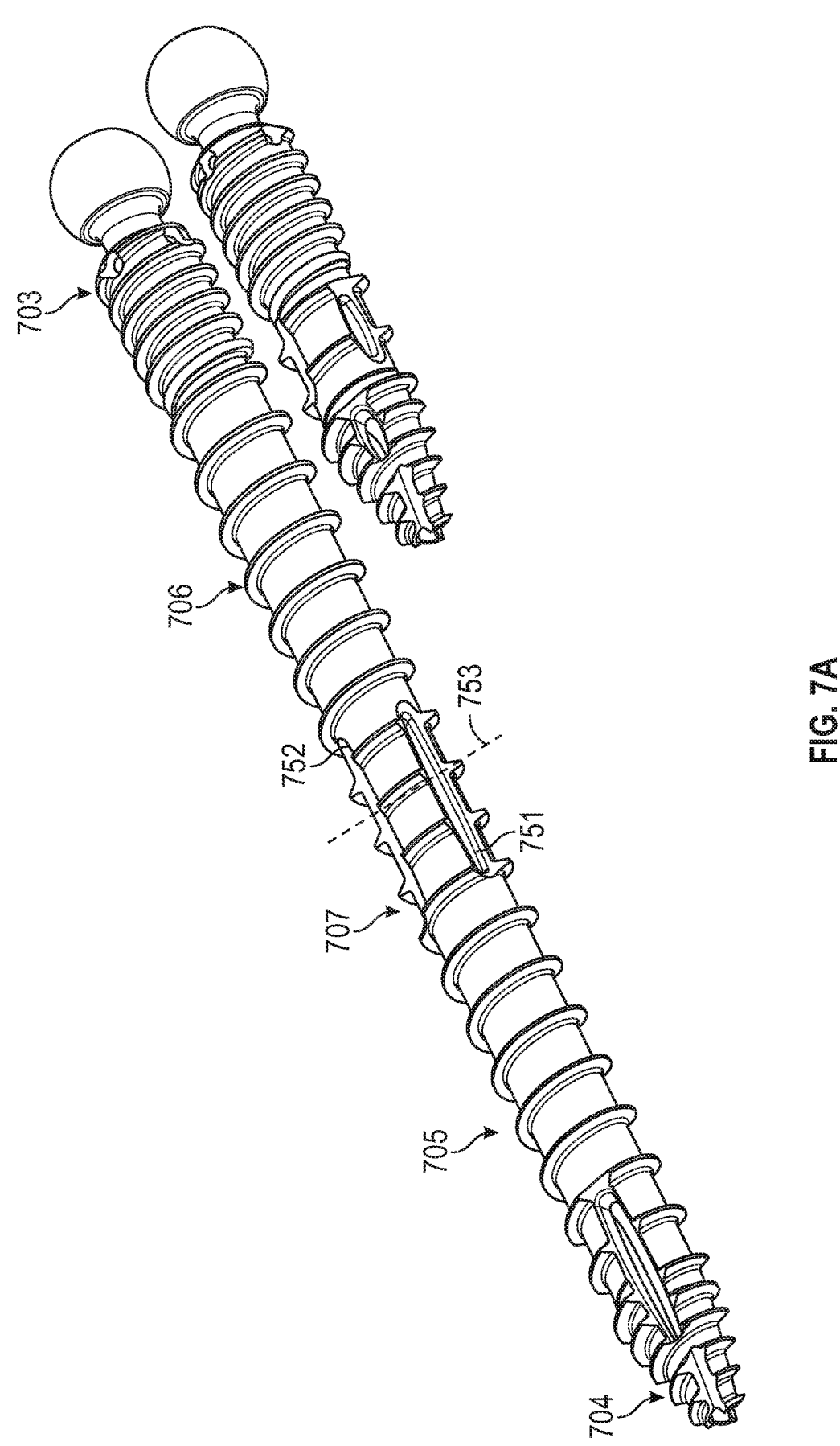
FIG. 7A shows a perspective view of long and short
versions of an embodiment.
Figure 7B:
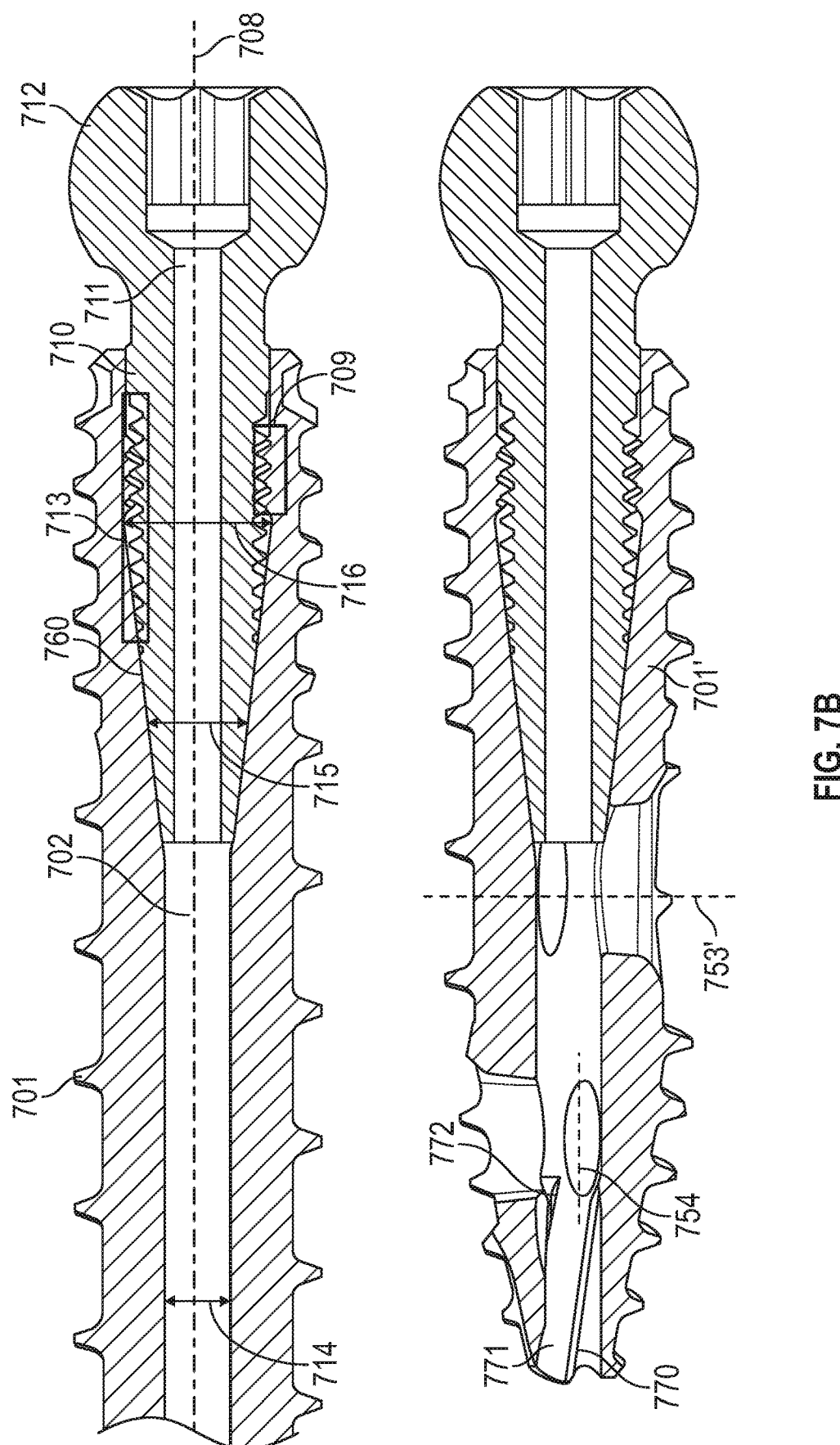
FIG. 7B shows a cross-sectional
view (partial) of the embodiments of FIG. 7A.
Figure 7C:
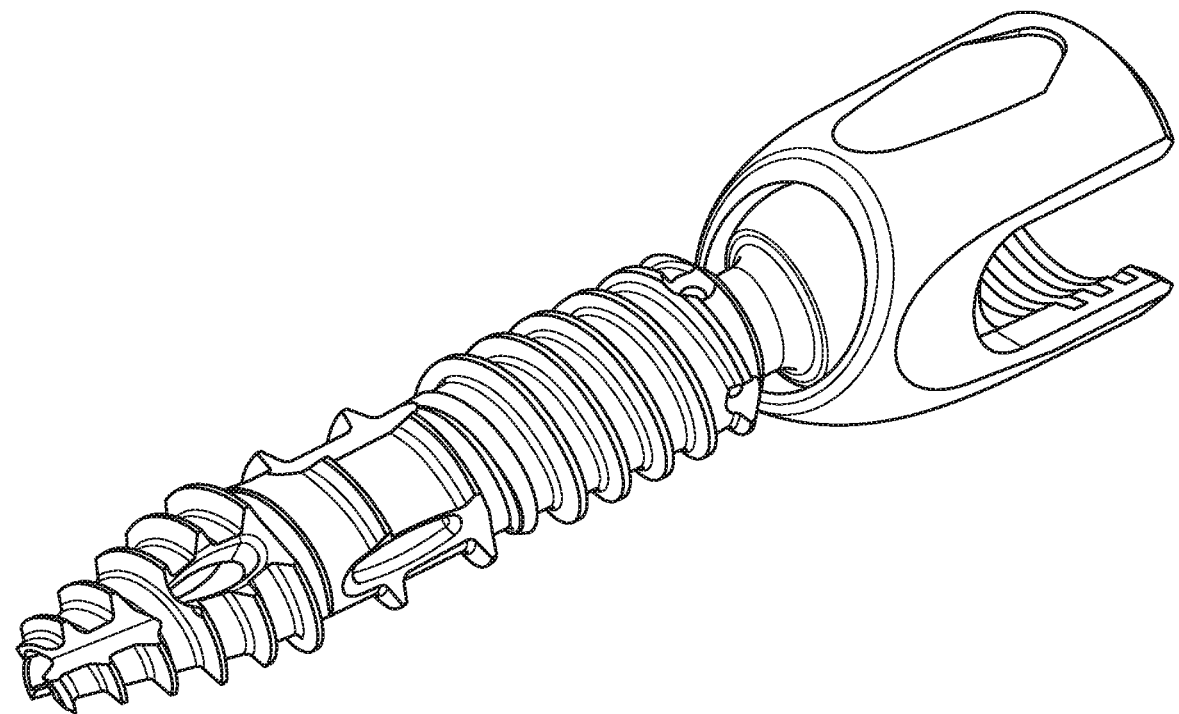
Figure 7D:
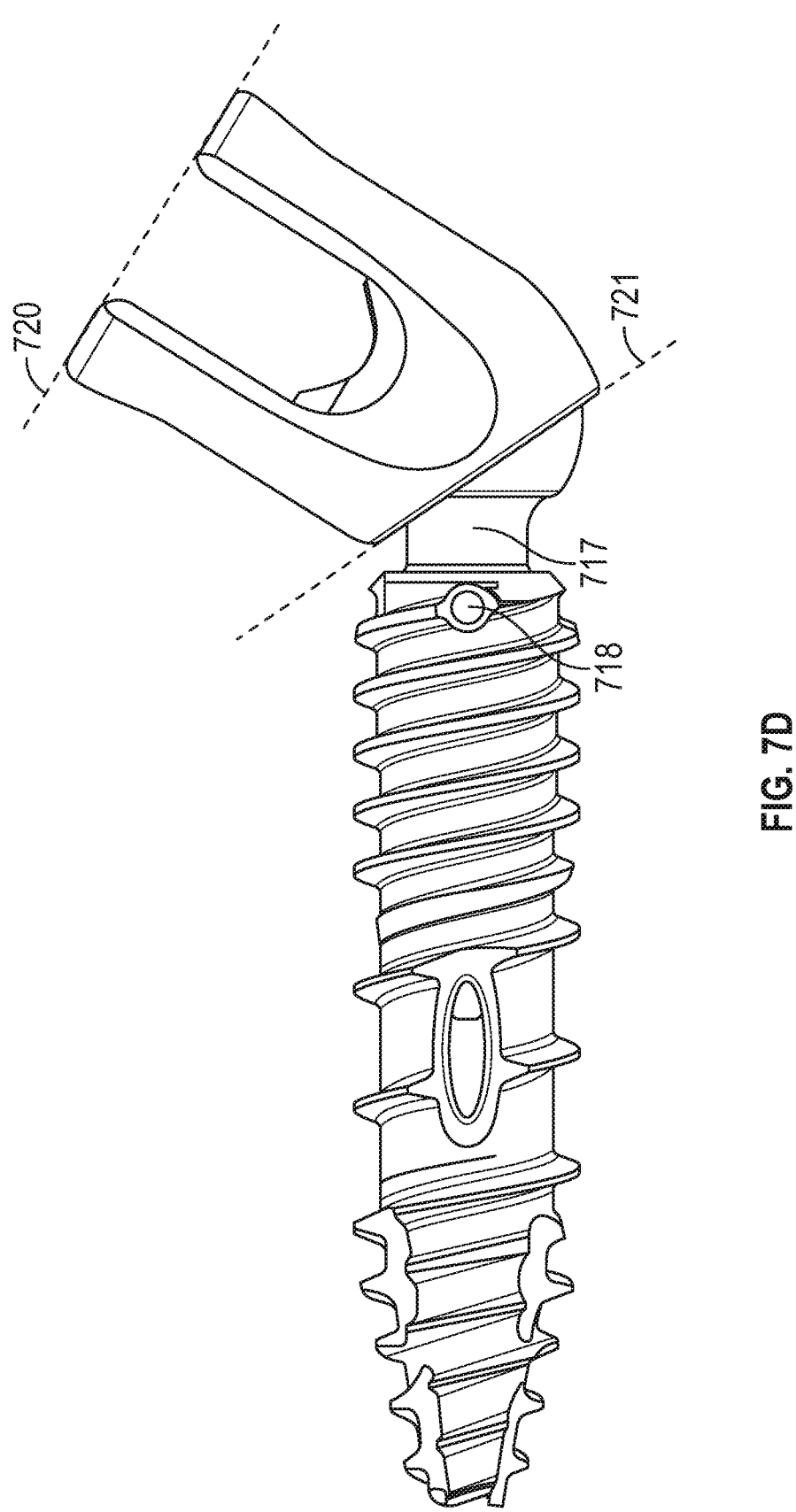
Figure 7E:
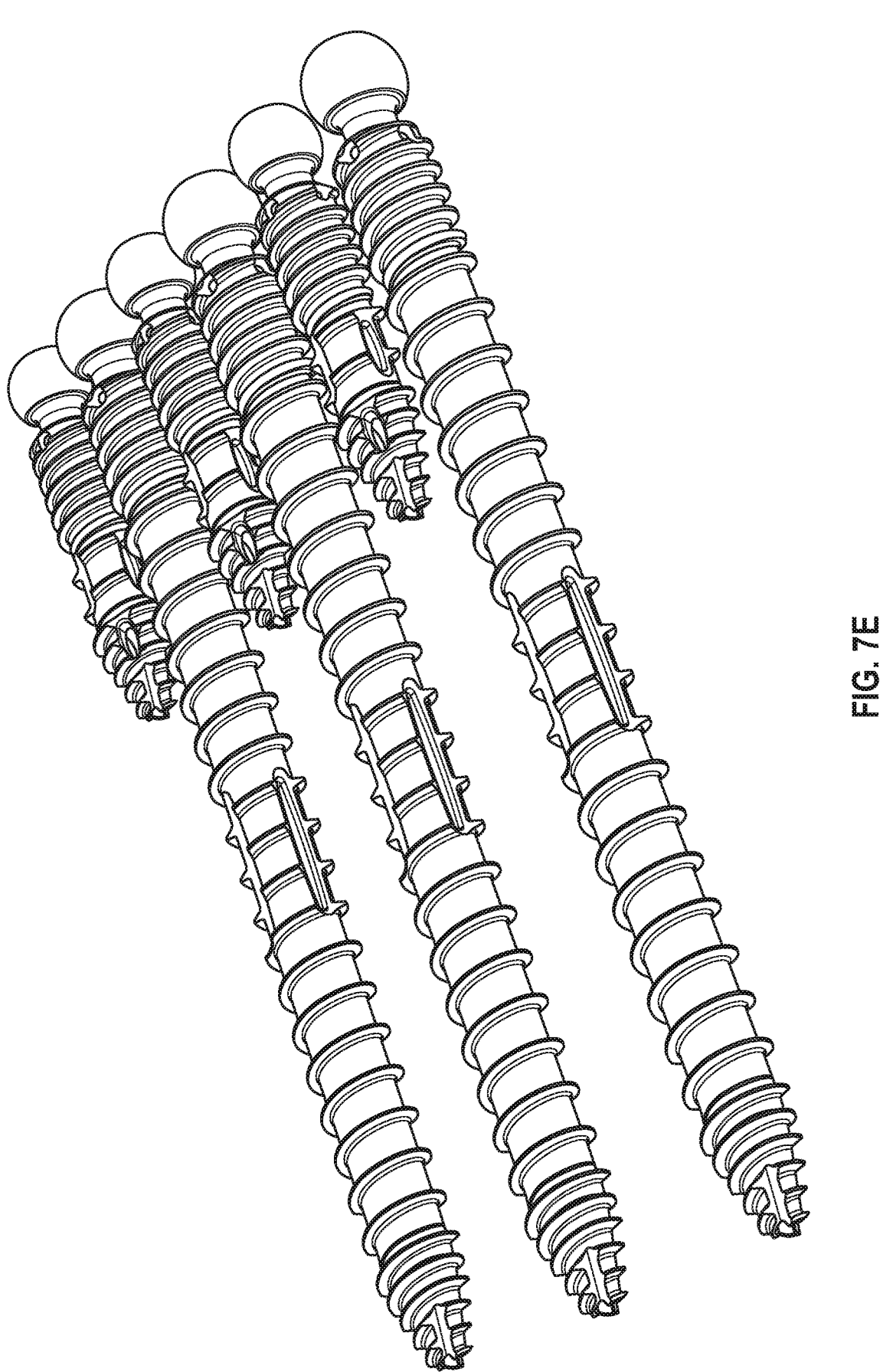
FIG. 7E
shows a series of short and long embodiments which may be
included in a kit.

For example, the transverse axis may align with diameter 715 of FIG. 7B. This tapering may add strength to the rod and prevent failure under high torque situations (as opposed to sudden changes in diameter such as 90-degree changes). In an embodiment, at least a portion of the rod tapers outwardly as it extends proximally. In an embodiment, at least a portion of the sleeve tapers outwardly as it extends proximally.

Example 8. The system according to any of Examples 1-3, wherein: the rod includes first, second, and third outer diameters; the first outer diameter is distal to the second and third outer diameters and the second outer diameter is between the first and third outer diameters; the second outer diameter is less than the third outer diameter.

In an embodiment, the first outer diameter is less than the second outer diameter. However, in other embodiments the diameter relationships are not so limited and may include more or fewer distinct outer diameters for the rod. For example, diameter 1 (714) may remain but diameter 2 (715) may extend proximally to end 703. In an embodiment, at least some of the inner diameters for the sleeve correspond to outer diameters for the rod. In other words, at least some of the inner and outer diameters generally match as shown in FIG. 7B.

Example 8.1 The system according to any of Examples 1 to 7, wherein the plurality of threads on the wall of the central sleeve channel are included entirely in a proximal third of the sleeve.

Example 9. The system according to any of Examples 1 to 8 comprising a tulip configured to substantially surround the head of the rod.

In an embodiment, the tulip includes a slot to slide around neck 717. However, in another embodiment the tulip may include resilient members which "pop" over head 712 and around neck 717. In another embodiment, the rod is slid through the distal aperture of the tulip and then into the sleeve. Afterwards, the rod and sleeve may be welded together at location 718 or may otherwise be fixedly coupled to each other and an interface between the rod and sleeve. The tulip may be coupled to the head at a manufacturing facility and then shipped to a clinic or the tulip may be joined to the head by the clinician at the clinic.

In an embodiment, the tulip may be used to couple the bone anchor system to a rod that affixes to additional tulips and bone anchors. Such as system may promote better load distribution among the spine to increase the lifespan of the implants. In other words, the coupling of the SI anchor system to vertebral anchor system may better distribute post-implant loading and lengthen the lifespan of the implant system and procedure.

Example 10. The system of Example 9, wherein: the tulip includes a distal surface and a proximal surface; the proximal surface provides an opening to a trough, the through being configured to receive a fusion rod; the distal surface includes an aperture to encircle at least a portion of the rod; the proximal surface is coplanar with a first plane (720) and the distal surface is coplanar with a second plane (721); the first and second planes are not parallel with each other.

Example 11. The system according to any of Examples 1-10, wherein the third portion is threaded.

Example 12. The system according to any of Examples 1 to 11, wherein the sleeve is a sacroiliac bone anchor.

Example 13. The system according to any of Examples 1 to 12, wherein: the first portion includes a first thread pitch for a majority of threads of the first portion; the second portion includes a second thread pitch for a majority of threads of the second portion; the first thread pitch is unequal to the second thread pitch.

As used herein, thread pitch is measured from the peak of one thread to the peak of an immediately adjacent thread, Example 14. The system of Example 13, wherein: the first thread pitch is larger than the second thread pitch; the first threaded portion is distal to the second threaded portion.

Example 15. The system of Example 14, wherein the outer sleeve is a compression screw.

As used herein, a compression screw compresses two articles against one another when the screw is drilled across a seam that exists between the two articles.

For example, differing thread pitches for areas 705, 706 result in a compression or lag screw that draws bone portions on either side of the SI joint towards each other in compression (i.e., one set of threads moves more quickly than another set of threads resulting in compression of adjacent bone portions). Smooth area 707 is configured to span the SI joint upon final implantation and its smoothness allows bone portions on either side of the SI joint to move/slide as fusion occurs over time.

Example 16. The system according to any of Examples 1 to 15, wherein: the sleeve is a non-milled conduit; the rod is a milled conduit.

Example 17. The system according to any of Examples 1 to 16, wherein the sleeve is a printed conduit.

Example 18. The system according to any of Examples 1 to 17, wherein: the sleeve includes projections on the outer surface of the sleeve; the projections are monolithic with the sleeve.

As used herein, "monolithic" means formed from a single piece without use of adhesives, welds, or other coupling agents or means.

Example 19. The system according to any of Examples 1 to 18, wherein the sleeve is welded to the rod.

For example, at least one weld may be located at location 718 (made via a hole formed in threads 706).

Example 20. The system according to any of Examples 1 to 18, wherein the sleeve is permanently and non-slidingly coupled to the rod.

For example, in an embodiment the sleeve is manufactured via a 3D printing process whereas the rod is manufactured via, for example, milling. As a result, the rod may have a higher strength with which to better tolerate torque and other forces experienced during implantation of the device and/or forces generated by the patient long after implantation. For example, high torque forces may be experienced at neck 717 during implantation of the system. However, the 3D process may allow for biocompatible surfaces that promote bone growth and better coupling between the implant and bone. For example, the surface of the sleeve may include irregular finger-like projections that are printed along with the rest of the sleeve with the projections and main conduit of the sleeve being monolithic with each other. Such projections may not be possible to form via a process such as milling.

In an embodiment, the sleeve is manufactured via additive manufacturing (e.g., 3D printing) while the rod is formed via milling. Then, at the manufacturing facility, the rod is forced into the sleeve and is retained within the sleeve via a resistance fit. In an embodiment, the rod is actually compressed radially by the sleeve. The system may be shipped to a clinical facility with the rod already inserted into the sleeve. In fact, in an embodiment the sleeve and rod are permanently coupled to each other via at least one weld. The clinician may then receive the already coupled sleeve and rod from a sterile package and proceed to implant the sleeve and rod simultaneously. As a result, the benefits of additive manufacturing (e.g., biocompatible surface) are delivered along with the benefits of more robust manufacturing (e.g., milled rod) that has strength to tolerate high torque forced experienced during implantation.

Example 21. The system according to any of Examples 1 to 20, wherein the central rod axis is coaxial with the central sleeve axis.

Example 22. The system according to any of Examples 1 to 21 comprising: an additional sleeve (701') that includes: (a) an additional central sleeve channel that traverses the additional sleeve and extends from a proximal end of the additional sleeve to a distal end of the additional sleeve, (b) an additional threaded first portion and an additional threaded second portion on an outer surface of the additional sleeve, (c) an additional third portion on the outer surface of the additional sleeve and existing between the additional first and second portions, (d) an additional central sleeve axis that extends from the proximal end of the additional sleeve to the distal end of the additional sleeve, and (e) an additional plurality of threads on a wall of the additional central sleeve channel; wherein: (a) the rod is proportioned to slide within the additional central sleeve channel, and (b) the plurality of threads on the outer surface of the rod are configured to screw into the additional plurality of threads on the wall of the additional central sleeve channel.

As shown in FIG. 7B, a single rod (or identical rods) can be used for sleeves of varying lengths. This decreases the amount of inventory needed to properly prepare of surgeries that may require short, long, or short and long outer sleeves.

Example 23. The system according to any of Examples 1 to 22, wherein: the sleeve includes titanium; the rod includes titanium.

Example 24. The system according to any of Examples 1-23, wherein an internal wall of the central sleeve channel includes a first ridge (770), a second ridge (772), and a trough (771) between the first and second ridges.

Such a trough may help funnel or direct bone particulate (e.g., created via drilling the sleeve or a wire) away from the distal entrance to the sleeve channel and towards apertures (e.g., aperture 751) to help promote bone fusion.

While various embodiments described herein address fixating a SI joint, other embodiments are not so limited and may be used generally to couple tissues together, such as two portions of bone or other tissue. Those portions need not be on opposite sides of a joint. For example, an anchor embodiment described herein could be used as a shank of a pedicle screw. Other embodiments may be used for surgery of the shoulder, wrist, toe (i.e., anywhere an implant is placed where bone is directed from one location to the internal flute of the implant to facilitate fusion).

Example Set C

Example 1. A bone anchor system comprising: a first sleeve (801) that includes: (a) a central first sleeve channel (802) that traverses the first sleeve and extends from a proximal end (803) to a distal end (804) of the first sleeve, and (b) a central first sleeve axis (708) that extends from the proximal end of the first sleeve to the distal end of the first sleeve, and a first rod (810) that includes: (a) a first central rod channel (811) that traverses the first rod and extends from a proximal end of the first rod to a distal end of the first rod, (b) a first head (812) on the proximal end of the first rod, the first head including a circular cross-section; (c) a first central rod axis that extends from the proximal end of the first rod to the distal end of the first rod, and (e) a first plurality of threads (813); a second rod (810') that includes: (a) a second central rod channel (811') that traverses the second rod and extends from a proximal end of the second rod to a distal end of the second rod, (b) a second head (812') on the distal end of the second rod; (c) a second central rod axis that extends from the proximal end of the second rod to the distal end of the second rod, and (e) a second plurality of threads (813'); wherein first, second, and third planes (851, 852, 853) are each orthogonal to the central first sleeve axis; wherein (a) the first plane intersects the second rod but not the first sleeve and not the first rod, (b) the second plane intersects the first rod and the first sleeve but not the second rod, and (a) the third plane intersects the first rod but not the first sleeve and not the second rod; wherein the first plurality of threads is directly coupled to the second plurality of threads.

Such an embodiment addresses "threads". One continuous/contiguous thread may be still be referred to herein as "threads" (plural). Further, an embodiment like FIG. 8D may depict some threads as male and others as female but those may be reversed in other embodiments.

Alternative version of Example 1. Example 1. A bone anchor system comprising: a first sleeve (801) that includes: (a) a central first sleeve channel (802) that traverses the first sleeve and extends from a proximal end (803) of the first sleeve to a distal end (804) of the first sleeve, and (b) a central first sleeve axis (708) that extends from the proximal end of the first sleeve to the distal end of the first sleeve, and a first rod (810) that includes: (a) a first central rod channel (811) that traverses the first rod and extends from a proximal end of the first rod to a distal end of the first rod; (b) a first central rod axis that extends from the proximal end of the first rod to the distal end of the first rod, and (c) a first plurality of threads (813); a second rod (810') that includes: (a) a second central rod channel (811') that traverses the second rod and extends from a proximal end of the second rod to a distal end of the second rod; (b) a second central rod axis that extends from the proximal end of the second rod to the distal end of the second rod, and (c) a second plurality of threads (813'); wherein first, second, and third planes (851, 852, 853) are each orthogonal to the central first sleeve axis; wherein (a) the first plane intersects the second rod but not the first sleeve and not the first rod, (b) the second plane intersects the first rod and the first sleeve but not the second rod, and (a) the third plane intersects the first rod but not the first sleeve and not the second rod; wherein the first plurality of threads is threadingly engaged with the second plurality of threads.

Thus embodiments may or may not have a head on either or both rods and the head may not be necessarily circular in cross-section.

Alternative version of Example 1. Example 1. A bone anchor system comprising: a first sleeve (801) that includes: (a) a central first sleeve channel (802) that traverses the first sleeve and extends from a proximal end (803) of the first sleeve to a distal end (804) of the first sleeve, and (b) a central first sleeve axis (708) that extends from the proximal end of the first sleeve to the distal end of the first sleeve, and a first rod (810) that includes: (a) a first central rod axis that extends from the proximal end of the first rod to the distal end of the first rod, and (b) a first plurality of threads (813); a second rod (810') that includes: (a) a second central rod axis that extends from the proximal end of the second rod to the distal end of the second rod, and (b) a second plurality of threads (813'); wherein first, second, and third planes (851, 852, 853) are each orthogonal to the central first sleeve axis; wherein (a) the first plane intersects the second rod but not the first sleeve and not the first rod, (b) the second plane intersects the first rod and the first sleeve but not the second rod, and (a) the third plane intersects the first rod but not the first sleeve and not the second rod; wherein the first plurality of threads is threadingly engaged with the second plurality of threads.

Thus, one or both rods may be cannulated in some embodiments and not cannulated in other embodiments. Further, having first and second rods does not necessarily exclude embodiments that may have a third rod (or more) coupled to the first and second rods.

Example 2. The system of example 1, wherein the first sleeve is compressed between the first and second rods.

In an embodiment, neither of the rods is compressed by the sleeve. For example, a void may exist between the sleeve and either or both of the first and second rods, thereby negating any radial force that could be exerted from the sleeve inward towards one or both rods.

Example 3. The system of example 1, wherein the first sleeve is compressed between the first and second rods based on the first plurality of threads being directly coupled to the second plurality of threads.

An advantage of the embodiment is as follows. The bolted construction (first and second rods being coupled to each other) puts the 3D printed sleeve in compression, which helps the sleeve achieve better fatigue resistance by offsetting tensile stresses. An embodiment ships to the consumer (e.g., physician, hospital, distributor) with the outer sleeve in compression because the distal and proximal cores/rods are already threaded to each other when shipped. The core/first rod, tip/second rod, and 3D printed sleeve are assembled, tightened, and then welded together before being shipped from the manufacturer. This causes the 3D printed sleeve to remain in a compressed state.

Example 4. The system of example 1, wherein: the first sleeve includes a first distal shoulder and a first proximal shoulder; the first rod includes a second proximal shoulder; the second rod includes a second distal shoulder; the first and second distal shoulders directly contact each other; the first and second proximal shoulders directly contact each other; the first plane intersects the second distal shoulder but not the first distal shoulder; the third plane intersects the second proximal shoulder but not the first proximal shoulder.

Example 5. The system of example 4, wherein the first sleeve is compressed between the second proximal and distal shoulders.

Figure 8A:
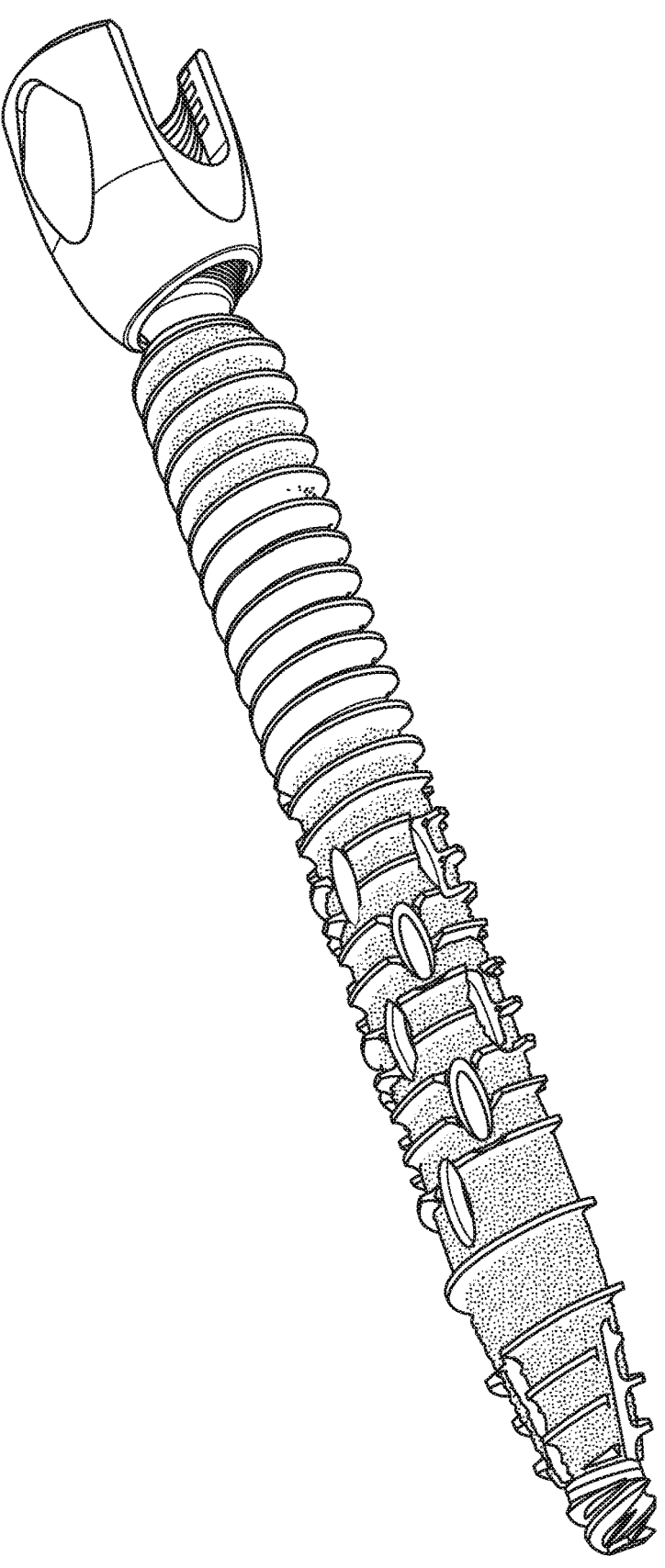
FIG. 8A provides a perspective view of an embodiment.
FIG. 8B provides a side view of the embodiment of FIG. 8A.
Figure 8B:
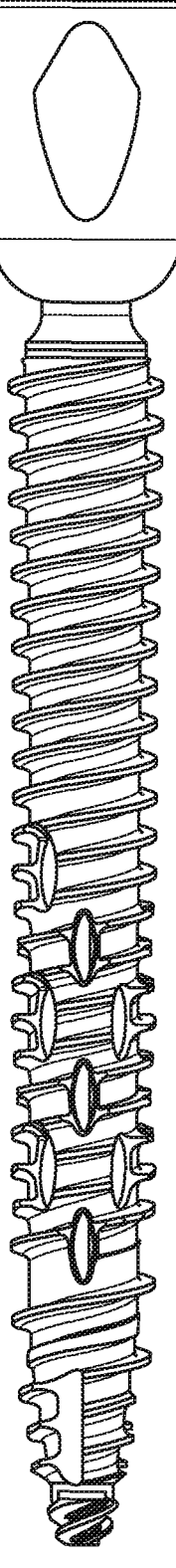
Figure 8C:
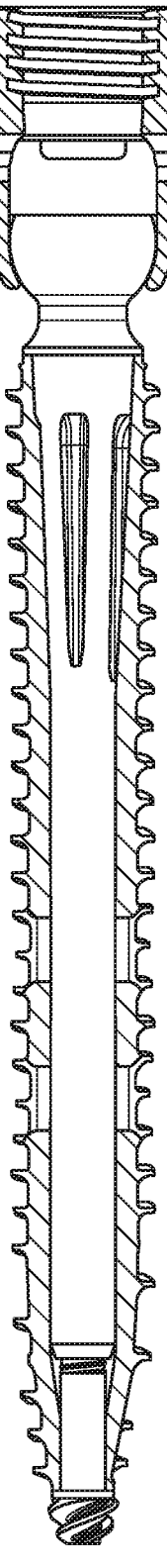
FIGS. 8C-8D provide cross-sectional views of portions of
the embodiment of FIG. 8A.
Figure 8D:
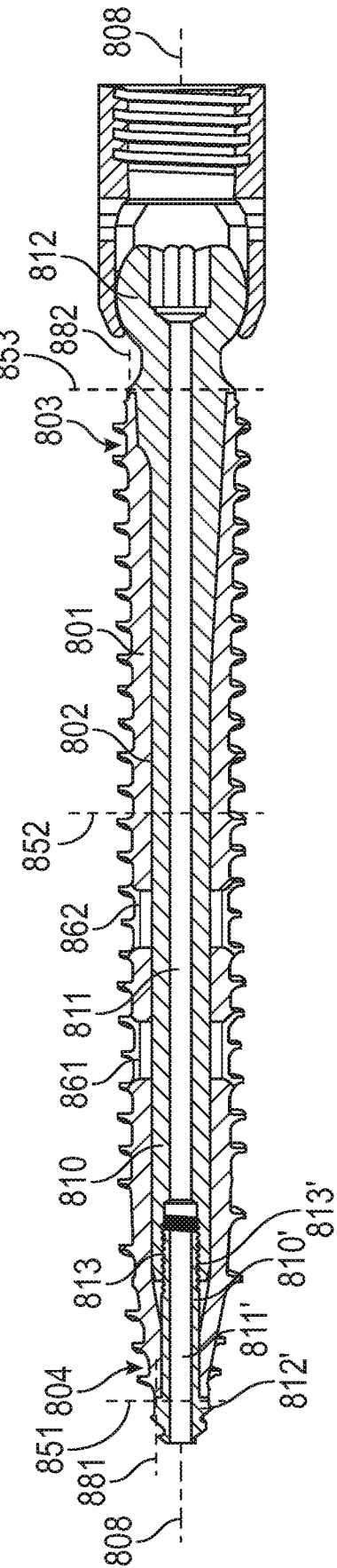
Figure 8E:
FIGS. 8E-8F provide exploded
views of the embodiment of FIG. 8A.
Figure 8E:
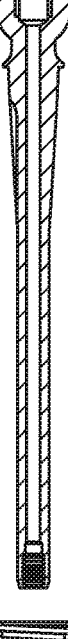
Figure 8E:
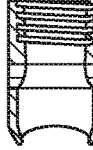
Figure 8E:
Figure 8F:
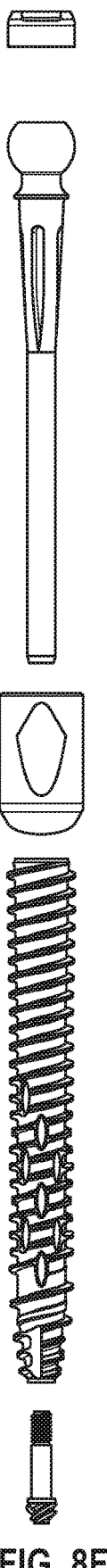
Figure 8G:
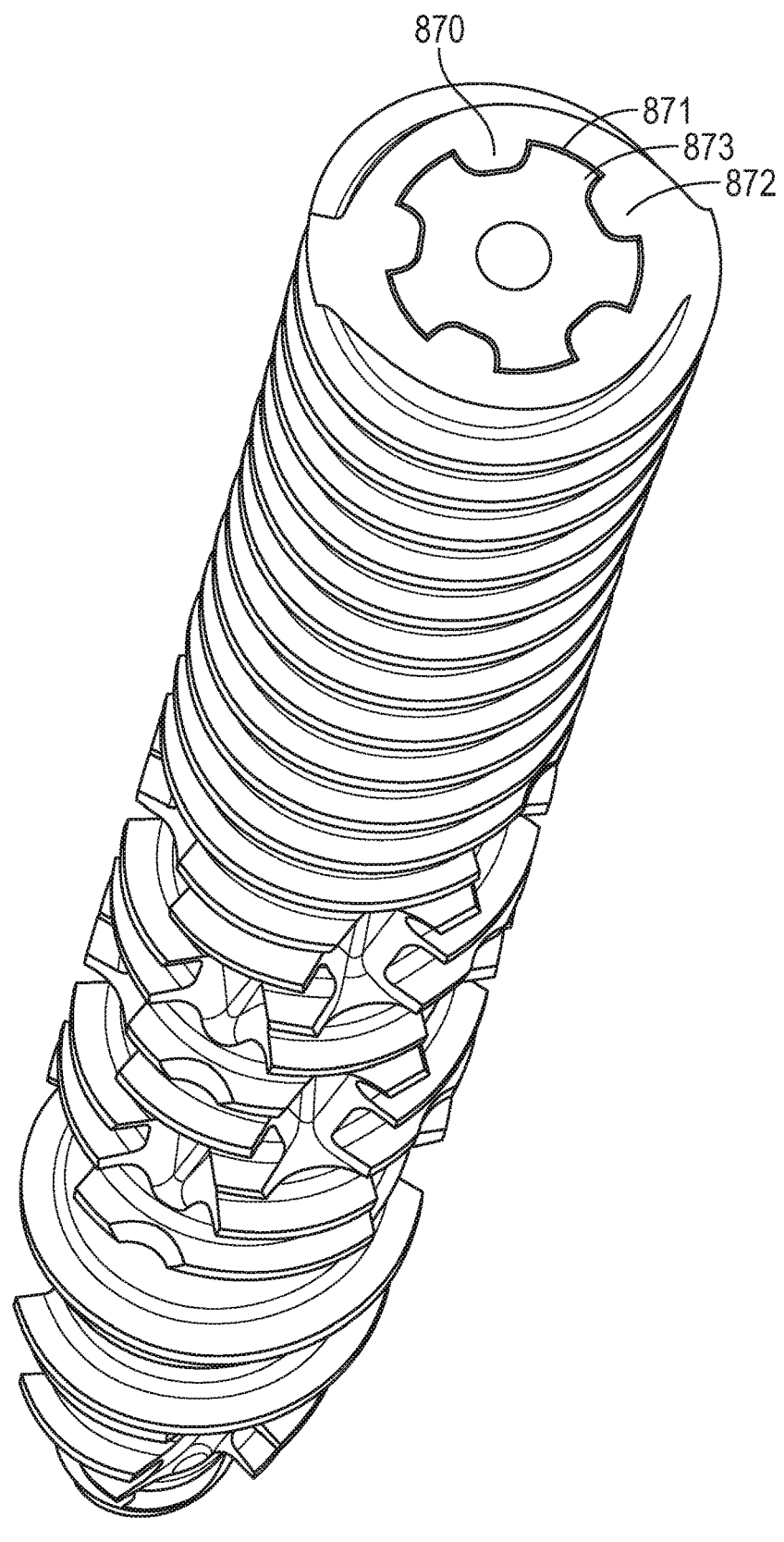
FIG. 8G provides a
cross-sectional view of the embodiment of FIG. 8A.

The shoulders may be outside and adjacent the proximal and distal ends of the outer sleeve in FIG. 8D. However, shoulders or flanges and the like could be internal to the sleeve and still facilitate compression of the sleeve as the rods are tightened to one another.

Example 6. The system of example 5, wherein: a first additional axis (881) is parallel to the central first sleeve axis and intersects the first and second distal shoulders; a second additional axis (882) is parallel to the central first sleeve axis and intersects the first and second proximal shoulders.

Example 7. The system of example 6, wherein: the first additional axis does not intersect the first and second proximal shoulders; the second additional axis does not intersect the first and second distal shoulders.

Example 8. The system according to any of examples 1 to 7, wherein: the sleeve is an additive manufactured conduit; the rod is milled.

As a result, the benefits of additive manufacturing/3D manufacturing (e.g., biocompatible surface) are delivered along with the benefits of more robust manufacturing (e.g., milled rod) that has strength to tolerate high torque force experienced during implantation.

Example 9. The system according to any of examples 1 to 8, wherein the central first sleeve channel is unthreaded.

This helps prevent unthreading of, for example, one or more core rods from the outer sleeve during high torque situations (e.g., anchor implantation).

Example 9. The system according to any of examples 1 to 8, wherein the central first sleeve channel is not threadingly coupled to either of the first or second rods.

Example 10. The system according to any of example 1-9 comprising: a second sleeve that includes: (a) a central second sleeve channel that traverses the second sleeve and extends from a proximal end of the second sleeve to a distal end of the second sleeve, and (b) a central second sleeve axis that extends from the proximal end of the second sleeve to the distal end of the second sleeve; wherein the central first sleeve channel is identically proportioned in length and varying widths to the central second sleeve channel; wherein the second sleeve has a maximum outer width that is wider than a maximum outer width of the first sleeve.

In an embodiment, the first and second rods are the same design for every screw diameter which improves manufacturability and reduces cost. Such rods can be paired with outer sleeves of varying sidewall thicknesses to provide users with options for varying anatomical situations without overly complicating the parts need for a properly sized anchor. Further, the modular nature of the assembly simplifies design iterations as the manufacture adds new sizes of the sleeve or changes the fenestration pattern on the sleeve. The modular nature of the assembly decreases the amount of inventory needed (by a hospital, distributor representative, etc.) to properly prepare of surgeries that may require anchors of varying widths.

While some embodiments include a head on the first rod, the modularity of the system provides other embodiments such as a headless system that is accomplished with the same out sleeve and second rod but merely changing the first rod structure.

Example 11. The system according to any of examples 1-10, wherein: an internal wall of the central first sleeve channel includes a first ridge (870), a second ridge (872), and a trough (871) between the first and second ridges; an external wall of the first rod includes third ridge (873) included within the trough.

In an embodiment, the splined interface between the 3D printed sleeve and the machined core (first rod) adds torsional stiffness to the assembly. The splined interface also prevents the core (first rod) from backing out of the 3D printed sleeve in the event of a weld failure. For example, if the proximal weld ever failed, the splines would continue to rotationally lock the core/first rod and 3D printed sleeve together to preventing the core/first rod from unthreading from the tip/second rod.

Example 12. The system of example 11, wherein: the first ridge is not a portion of a thread and does not curve about the central first sleeve axis; the second ridge is not a portion of a thread and does not curve about the central first sleeve axis; the third ridge is not a portion of a thread and does not curve about the central first sleeve axis.

Such an arrangement may have advantages over, for example, spiral splines interlocking the machined core/first rod to the 3D printed body with large spot welds. The lack of spiraling of the splines helps prevent unscrewing of components (e.g., between the first and second rods) and failure of the anchor under torque loads.

Example 13. The system according to any of examples 1 to 12 comprising a tulip substantially surrounding the first head of the first rod, wherein: the tulip includes a distal surface and a proximal surface; the proximal surface provides an opening to a trough, the trough being configured to receive a fusion rod; the distal surface includes an aperture encircling at least a portion of the rod; the aperture has a maximum width that is smaller than a maximum width of the first head.

Example 14. The system according to any of examples 1-13, wherein: the first sleeve includes first and second apertures (861, 862) in a sidewall of the sleeve; the first aperture includes a long axis parallel to the central first sleeve axis; the first aperture includes a short axis orthogonal to the long axis of the first aperture; the first aperture includes a length measured along the long axis of the first aperture and a width measured along the short axis of the first aperture; the length of the first aperture is greater than the width of the first aperture.

Example 15. The system according to any of examples 1 to 14, wherein: the first sleeve includes a proximal third portion, a distal third portion, and a middle third portion between the proximal and distal third portions; the proximal third portion includes a first thread pitch for a majority of the threads of the proximal third portion; the distal portion includes a second thread pitch for a majority of the threads of the distal portion; the first thread pitch is less than the second thread pitch.

Example 16. The system according to any of examples 1 to 15, wherein the first sleeve is welded to the first rod.

Example 17. The system of example 16 wherein the first sleeve is welded to the second rod.

Example 18. The system according to any of examples 1 to 15, wherein the first sleeve is permanently and non-slidingly coupled to the first rod and to the second rod.

For example, instead of or in addition to a weld, an adhesive or other coupling mechanism may couple the sleeve to one or both rods.

Example 19. The system according to any of examples 1-18, wherein the second rod includes a third plurality of threads (813") located distal to the second plurality of threads (813') and distal to the first sleeve.

Example 20. The system of example 19, wherein the second plurality of threads is non-contiguous with the third plurality of threads.

For example, in FIG. 8D the second rod has a non-threaded area between threads on either of the second rod's opposing ends.

Example 21. The system of example 19, wherein: the first plurality of threads includes at least one fluted portion (863, 864); the second plurality of threads is unfluted.

Figure 8H:
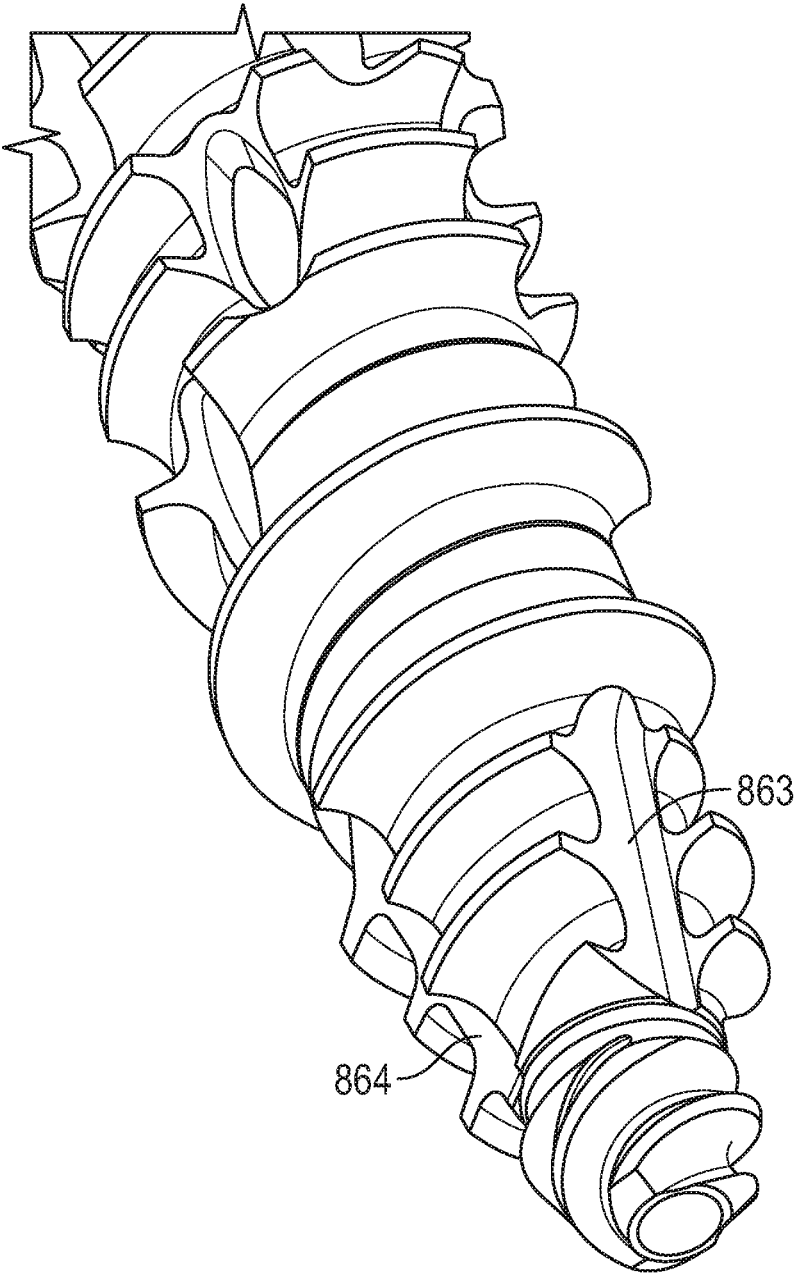
Figure 8I:
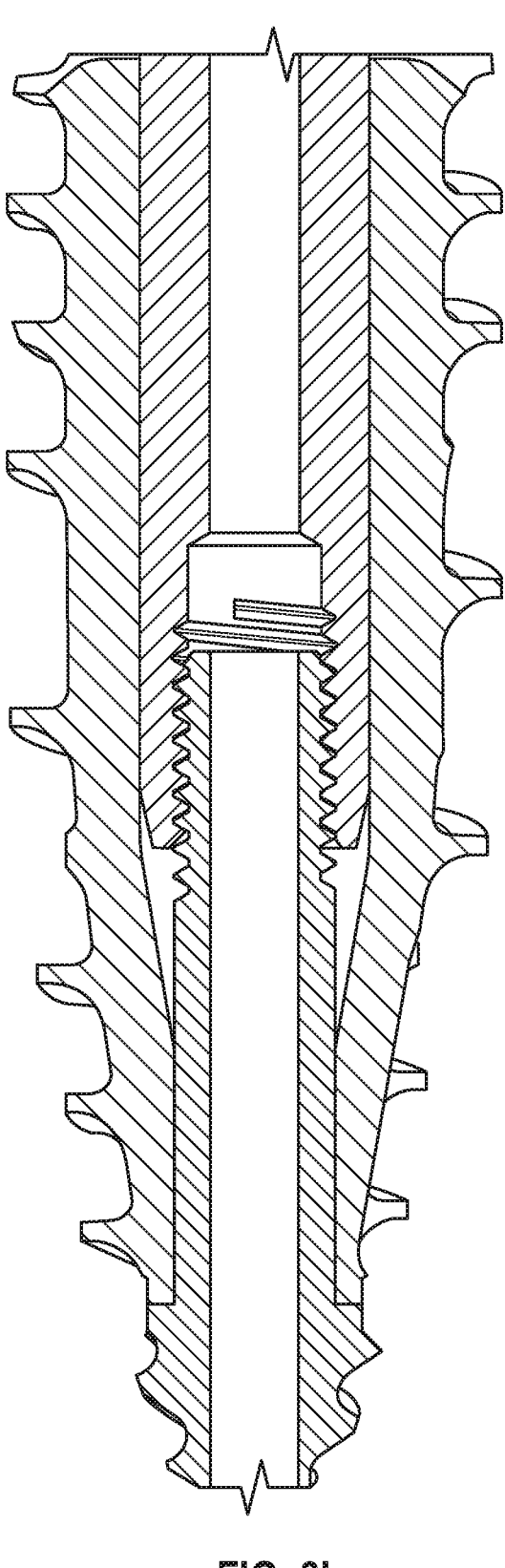
FIG. 8I provides a close up
cross-sectional view of a distal end of the embodiment of
FIG. 8A.
Figure 9:
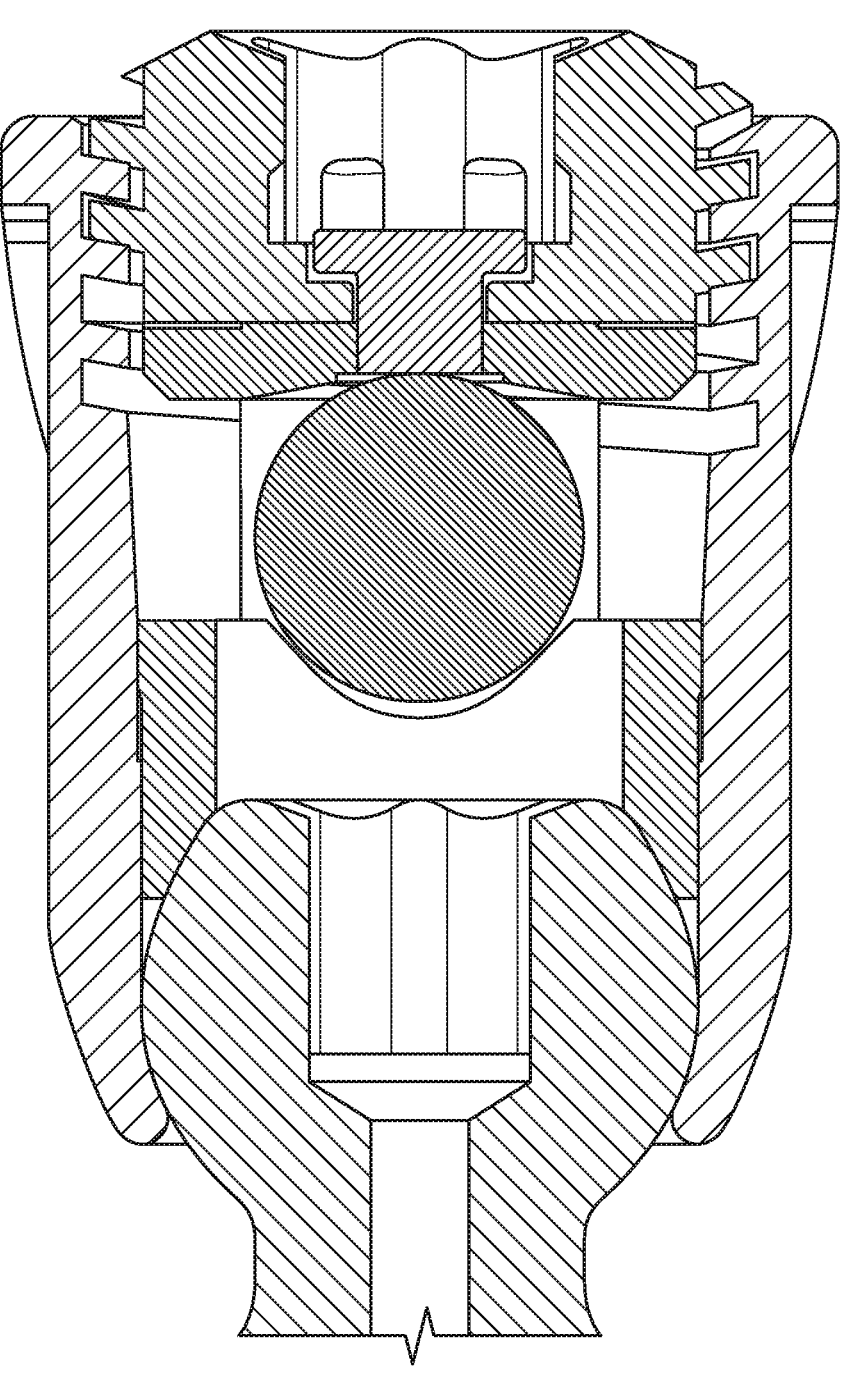
FIG. 9 provides a cross-sectional view of the tulip and saddle of the embodiment of FIG. 8A.

As shown in FIG. 8H, the sleeve has cutting flutes but the distal core lacks flutes. In an embodiment, the distal core lacks any specific clocking to the sleeve so any flutes on the distal core would not reliably align with flutes on the sleeve. However, other embodiments may include flutes on the distal core and the sleeve wherein the flutes align with each other.

Example 22. The system according to any of examples 1-21, wherein the second rod is a bolt.

As used herein, a bolt is a rod or pin for fastening objects together that may have a head at one end and threads at the other (the threads to be secured by a nut or other component). For example, the first rod functions as a nut in FIG. 8D for the bolt/second rod.

Thus, the second rod acts as both a leading tip for the anchor and a bolt that results in compress of the outer sleeve. In an embodiment, a weld between the tip/second rod and the 3D printed body keeps prevents system failure under heavy and/or spontaneous torque loads.

Example 23. A method of assembling a bone anchor system, the method comprising: providing a first sleeve (801) that includes: (a) a central first sleeve channel (802) that traverses the first sleeve and extends from a proximal end (803) of the first sleeve to a distal end (804) of the first sleeve, and (b) a central first sleeve axis (708) that extends from the proximal end of the first sleeve to the distal end of the first sleeve, and inserting a first rod (810) into the first sleeve, the first rod including: (a) a first central rod channel (811) that traverses the first rod and extends from a proximal end of the first rod to a distal end of the first rod, (b) a first head (812) on the proximal end of the first rod, the first head including a circular cross-section; (c) a first central rod axis that extends from the proximal end of the first rod to the distal end of the first rod, and (e) a first plurality of threads (813); inserting a second rod (810') into the first sleeve, the second rod including: (a) a second central rod channel (811') that traverses the second rod and extends from a proximal end of the second rod to a distal end of the second rod, (b) a second head (812') on the distal end of the second rod; (c) a second central rod axis that extends from the proximal end of the second rod to the distal end of the second rod, and (e) a second plurality of threads (813'); screwing the first plurality of threads to the second plurality of threads to compress the first sleeve between the first and second rods; wherein first, second, and third planes (851, 852, 853) are each orthogonal to the central first sleeve axis; wherein (a) the first plane intersects the second rod but not the first sleeve and not the first rod, (b) the second plane intersects the first rod and the first sleeve but not the second rod, and (a) the third plane intersects the first rod but not the first sleeve and not the second rod.

Example 24. The method of example 23 comprising permanently and non-slidingly coupling the first sleeve to at least one of the first rod, the second rod, or combinations thereof after screwing the first plurality of threads to the second plurality of threads to compress the first sleeve between the first and second rods.

In an embodiment, the first rod is passed through a 3D printed body/sleeve and then a second rod, that acts as a bolt, is threaded into the first rod to compress the sleeve. The rods are then welded in at two places collectively to each end of the 3D printed body to keep the rods from unthreading from the sleeve. This assembly method creates a very strong screw assembly.

Embodiments addressed herein prevent the tulip from dislodging from the ball of the screw core/first rod. For example, in FIG. 8D the sleeve is not attached to the tulip with a thread. A threaded connection may unthread under certain conditions (e.g., increased resistance from tissue during anchor implantation) causing the tulip to disassociate from the sleeve. In FIG. 8D the tulip is captured by the ball on the end of the core/first rod as the screw is assembled.

When the screw tip/second rod, core/first rod, and 3D printed body are welded together the tulip can no longer be removed.

Example 25. The method of example 24 wherein permanently and non-slidingly coupling the first sleeve to at least one of the first rod, the second rod, or combinations thereof includes welding the first sleeve to the first rod.

Example 26. The method according to any of examples 24-25, wherein permanently and non-slidingly coupling the first sleeve to at least one of the first rod, the second rod, or combinations thereof includes welding the first sleeve to the second rod.

Example 27. The method according to any of examples 23-26, wherein the bone anchor system includes the bone anchor system according to any of examples 1-22.

Example Set D

Example 1. A bone anchor system comprising: a first outer conduit (801) that includes: (a) a central first outer conduit channel (802) that traverses the first outer conduit and extends from a proximal end (803) of the first outer conduit to a distal end (804) of the first outer conduit, and (b) a central first outer conduit axis (708) that extends from the proximal end of the first outer conduit to the distal end of the first outer conduit, and a first core conduit (810) that includes: (a) a first central core conduit channel (811) that traverses the first core conduit and extends from a proximal end of the first core conduit to a distal end of the first core conduit, (b) a first head (812) on the proximal end of the first core conduit, the first head including a circular cross-section; (c) a first central core conduit axis that extends from the proximal end of the first core conduit to the distal end of the first core conduit, and (e) a first plurality of threads (813); a second core conduit (810') that includes: (a) a second central core conduit channel (811') that traverses the second core conduit and extends from a proximal end of the second core conduit to a distal end of the second core conduit, (b) a second head (812') on the distal end of the second core conduit; (c) a second central core conduit axis that extends from the proximal end of the second core conduit to the distal end of the second core conduit, and (e) a second plurality of threads (813'); wherein first, second, and third planes (851, 852, 853) are each orthogonal to the central first outer conduit axis; wherein (a) the first plane intersects the second core conduit but not the first outer conduit and not the first core conduit, (b) the second plane intersects the first core conduit and the first outer conduit but not the second core conduit, and (a) the third plane intersects the first core conduit but not the first outer conduit and not the second core conduit; wherein the first plurality of threads is directly coupled to the second plurality of threads.

Example 2. The system of example 1, wherein the first outer conduit is compressed between the first and second core conduits.

Example 3. The system of example 1, wherein the first outer conduit is compressed between the first and second core conduits based on the first plurality of threads being directly coupled to the second plurality of threads.

Example 4. The system of example 1, wherein: the first outer conduit includes a first distal shoulder and a first proximal shoulder; the first core conduit includes a second proximal shoulder; the second core conduit includes a second distal shoulder; the first and second distal shoulders directly contact each other; the first and second proximal shoulders directly contact each other; the first plane intersects the second distal shoulder but not the first distal shoulder; the third plane intersects the second proximal shoulder but not the first proximal shoulder.

Example 5. The system of example 4, wherein the first outer conduit is compressed between the second proximal and distal shoulders.

Example 6. The system of example 5, wherein: a first additional axis (881) is parallel to the central first outer conduit axis and intersects the first and second distal shoulders; a second additional axis (882) is parallel to the central first outer conduit axis and intersects the first and second proximal shoulders.

Example 7. The system of example 6, wherein: the first additional axis does not intersect the first and second proximal shoulders; the second additional axis does not intersect the first and second distal shoulders.

Example 8. The system according to any of examples 1 to 7, wherein: the outer conduit is an additive manufactured outer conduit; the core conduit is milled.

Example 9. The system according to any of examples 1 to 8, wherein the central first outer conduit channel is unthreaded.

Example 10. The system according to any of example 1-9 comprising: a second outer conduit that includes: (a) a central second outer conduit channel that traverses the second outer conduit and extends from a proximal end of the second outer conduit to a distal end of the second outer conduit, and (b) a central second outer conduit axis that extends from the proximal end of the second outer conduit to the distal end of the second outer conduit; wherein the central first outer conduit channel is identically proportioned in length and varying widths to the central second outer conduit channel; wherein the second outer conduit has a maximum outer width that is wider than a maximum outer width of the first outer conduit.

Example 11. The system according to any of examples 1-10, wherein: an internal wall of the central first outer conduit channel includes a first ridge (870), a second ridge (872), and a trough (871) between the first and second ridges; an external wall of the first core conduit includes third ridge (873) included within the trough.

Example 12. The system of example 11, wherein: the first ridge is not a portion of a thread and does not curve about the central first outer conduit axis; the second ridge is not a portion of a thread and does not curve about the central first outer conduit axis; the third ridge is not a portion of a thread and does not curve about the central first outer conduit axis.

Example 13. The system according to any of examples 1 to 12 comprising a tulip substantially surrounding the first head of the first core conduit, wherein: the tulip includes a distal surface and a proximal surface; the proximal surface provides an opening to a trough, the trough being configured to receive a fusion core conduit; the distal surface includes an aperture encircling at least a portion of the core conduit; the aperture has a maximum width that is smaller than a maximum width of the first head.

Example 14. The system according to any of examples 1-13, wherein: the first outer conduit includes first and second apertures (861, 862) in a sidewall of the outer conduit; the first aperture includes a long axis parallel to the central first outer conduit axis; the first aperture includes a short axis orthogonal to the long axis of the first aperture; the first aperture includes a length measured along the long axis of the first aperture and a width measured along the short axis of the first aperture; the length of the first aperture is greater than the width of the first aperture.

Example 15. The system according to any of examples 1 to 14, wherein: the first outer conduit includes a proximal third portion, a distal third portion, and a middle third portion between the proximal and distal third portions; the proximal third portion includes a first thread pitch for a majority of the threads of the proximal third portion; the distal portion includes a second thread pitch for a majority of the threads of the distal portion; the first thread pitch is less than the second thread pitch.

Example 16. The system according to any of examples 1 to 15, wherein the first outer conduit is welded to the first core conduit.

Example 17. The system of example 16 wherein the first outer conduit is welded to the second core conduit.

Example 18. The system according to any of examples 1 to 15, wherein the first outer conduit is permanently and non-slidingly coupled to the first core conduit and to the second core conduit.

Example 19. The system according to any of examples 1-18, wherein the second core conduit includes a third plurality of threads (813") located distal to the second plurality of threads (813') and distal to the first outer conduit.

Example 20. The system of example 19, wherein the second plurality of threads is non-contiguous with the third plurality of threads.

Example 21. The system of example 19, wherein: the first plurality of threads includes at least one fluted portion (863, 864); the second plurality of threads is unfluted.

Example 22. The system according to any of examples 1-21, wherein the second core conduit is a bolt.

Example 23. A method of assembling a bone anchor system, the method comprising: providing a first outer conduit (801) that includes: (a) a central first outer conduit channel (802) that traverses the first outer conduit and extends from a proximal end (803) of the first outer conduit to a distal end (804) of the first outer conduit, and (b) a central first outer conduit axis (708) that extends from the proximal end of the first outer conduit to the distal end of the first outer conduit, and inserting a first core conduit (810) into the first outer conduit, the first core conduit including: (a) a first central core conduit channel (811) that traverses the first core conduit and extends from a proximal end of the first core conduit to a distal end of the first core conduit, (b) a first head (812) on the proximal end of the first core conduit, the first head including a circular cross-section; (c) a first central core conduit axis that extends from the proximal end of the first core conduit to the distal end of the first core conduit, and (e) a first plurality of threads (813); inserting a second core conduit (810') into the first outer conduit, the second core conduit including: (a) a second central core conduit channel (811') that traverses the second core conduit and extends from a proximal end of the second core conduit to a distal end of the second core conduit, (b) a second head (812') on the distal end of the second core conduit; (c) a second central core conduit axis that extends from the proximal end of the second core conduit to the distal end of the second core conduit, and (e) a second plurality of threads (813'); screwing the first plurality of threads to the second plurality of threads to compress the first outer conduit between the first and second core conduits; wherein first, second, and third planes (851, 852, 853) are each orthogonal to the central first outer conduit axis; wherein (a) the first plane intersects the second core conduit but not the first outer conduit and not the first core conduit, (b) the second plane intersects the first core conduit and the first outer conduit but not the second core conduit, and (a) the third plane intersects the first core conduit but not the first outer conduit and not the second core conduit.

Example 24. The method of example 23 comprising permanently and non-slidingly coupling the first outer conduit to at least one of the first core conduit, the second core conduit, or combinations thereof after screwing the first plurality of threads to the second plurality of threads to compress the first outer conduit between the first and second core conduits.

Example 25. The method of example 24 wherein permanently and non-slidingly coupling the first outer conduit to at least one of the first core conduit, the second core conduit, or combinations thereof includes welding the first outer conduit to the first core conduit.

Example 26. The method according to any of examples 24-25, wherein permanently and non-slidingly coupling the first outer conduit to at least one of the first core conduit, the second core conduit, or combinations thereof includes welding the first outer conduit to the second core conduit.

Example 27. The method according to any of examples 23-26, wherein the bone anchor system includes the bone anchor system according to any of examples 1-22.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a certain side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first article "on" a second article is directly on and in immediate contact with the second article unless such is specifically stated; there may be a third article or other structure between the first article and the second article on the first article. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A bone anchor system comprising:
   a first sleeve that includes: (a) a central first sleeve channel that traverses the first sleeve and extends from a proximal end of the first sleeve to a distal end of the first sleeve, and (b) a central first sleeve axis that extends from the proximal end of the first sleeve to the distal end of the first sleeve, and
   a first rod that includes: (a) a first central rod channel that traverses the first rod and extends from a proximal end of the first rod to a distal end of the first rod, (b) a first head on the proximal end of the first rod, the first head including a circular cross-section; (c) a first central rod axis that extends from the proximal end of the first rod to the distal end of the first rod, and (d) a first plurality of threads;
   a second rod that includes: (a) a second central rod channel that traverses the second rod and extends from a proximal end of the second rod to a distal end of the second rod, (b) a second head on the distal end of the second rod; (c) a second central rod axis that extends from the proximal end of the second rod to the distal end of the second rod, and (d) a second plurality of threads;

wherein first, second, and third planes are each orthogonal to the central first sleeve axis;

wherein (a) the first plane intersects the second rod but not the first sleeve and not the first rod, (b) the second plane intersects the first rod and the first sleeve but not the second rod, and (c) the third plane intersects the first rod but not the first sleeve and not the second rod;

wherein the first plurality of threads is directly coupled to the second plurality of threads;

wherein the first sleeve includes a first distal shoulder and a first proximal shoulder;

wherein the first rod includes a second proximal shoulder and the second rod includes a second distal shoulder;

wherein the first and second distal shoulders directly contact each other and the first and second proximal shoulders directly contact each other;

wherein the first plane intersects the second distal shoulder but not the first distal shoulder and the third plane intersects the second proximal shoulder but not the first proximal shoulder.

2. The system of claim 1, wherein the first sleeve is compressed between the first and second rods.

3. The system of claim 1, wherein the first sleeve is compressed between the first and second rods based on the first plurality of threads being directly coupled to the second plurality of threads.

4. The system of claim 1, wherein the first sleeve is compressed between the second proximal and distal shoulders.

5. The system of claim 4, wherein:

a first additional axis is parallel to the central first sleeve axis and intersects the first and second distal shoulders;

a second additional axis is parallel to the central first sleeve axis and intersects the first and second proximal shoulders.

6. The system of claim 5, wherein:

the first additional axis does not intersect the first and second proximal shoulders;

the second additional axis does not intersect the first and second distal shoulders.

7. The system of claim 1, wherein:

the first sleeve is an additive manufactured conduit;

the first rod is milled.

8. The system of claim 1, wherein the central first sleeve channel is unthreaded.

9. The system of claim 1 comprising:

a second sleeve that includes: (a) a central second sleeve channel that traverses the second sleeve and extends from a proximal end of the second sleeve to a distal end of the second sleeve, and (b) a central second sleeve axis that extends from the proximal end of the second sleeve to the distal end of the second sleeve;

wherein the central first sleeve channel is identically proportioned in length and varying widths to the central second sleeve channel wherein the second sleeve has a maximum outer width that is wider than a maximum outer width of the first sleeve.

10. The system of claim 1, wherein:

an internal wall of the central first sleeve channel includes a first ridge, a second ridge, and a trough between the first and second ridges;

an external wall of the first rod includes third ridge included within the trough.

11. The system of claim 10, wherein:

the first ridge is not a portion of a thread and does not curve about the central first sleeve axis;

the second ridge is not a portion of a thread and does not curve about the central first sleeve axis;

the third ridge is not a portion of a thread and does not curve about the central first sleeve axis.

12. The system of claim 1 comprising a tulip coupled to the first head of the first rod, wherein:

the tulip includes a distal surface and a proximal surface;

the proximal surface provides an opening to a trough, the trough being configured to receive a fusion rod;

the distal surface includes an aperture encircling at least a portion of the first rod;

the aperture has a maximum width that is smaller than a maximum width of the first head.

13. The system of claim 1, wherein:

the first sleeve includes first and second apertures in a sidewall of the first sleeve;

the first aperture includes a long axis parallel to the central first sleeve axis;

the first aperture includes a short axis orthogonal to the long axis of the first aperture;

the first aperture includes a length measured along the long axis of the first aperture and a width measured along the short axis of the first aperture;

the length of the first aperture is greater than the width of the first aperture.

14. The system of claim 1, wherein:

the first sleeve includes a proximal third portion, a distal third portion, and a middle third portion between the proximal and distal third portions;

the proximal third portion includes a first thread pitch for a majority of the threads of the proximal third portion;

the distal third portion includes a second thread pitch for a majority of the threads of the distal third portion;

the first thread pitch is less than the second thread pitch.

15. The system of claim 1, wherein the first sleeve is welded to the first rod.

16. The system of claim 15 wherein the first sleeve is welded to the second rod.

17. The system of claim 1, wherein the first sleeve is permanently and non-slidingly coupled to the first rod and to the second rod.

18. The system of claim 1, wherein the second rod includes a third plurality of threads located distal to the second plurality of threads and distal to the first sleeve.

19. The system of claim 18, wherein the second plurality of threads is non-contiguous with the third plurality of threads.

20. The system of claim 18, wherein:

the first plurality of threads includes at least one fluted portion;

the second plurality of threads is unfluted.

21. The system of claim 1, wherein the second rod is a bolt.

* * * * *